(12) United States Patent
Enzmann et al.

(10) Patent No.: US 9,471,973 B2
(45) Date of Patent: Oct. 18, 2016

(54) METHODS AND APPARATUS FOR COMPUTER-AIDED RADIOLOGICAL DETECTION AND IMAGING

(71) Applicant: THE REGENTS OF THE UNIVERSITY OF CALIFORNIA, Oakland, CA (US)

(72) Inventors: Dieter R. Enzmann, Los Angeles, CA (US); Matthew S. Brown, Los Angeles, CA (US); Jonathan Goldin, Los Angeles, CA (US); Bharath Ramakrishna, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 46 days.

(21) Appl. No.: 13/953,543

(22) Filed: Jul. 29, 2013

(65) Prior Publication Data

US 2013/0322725 A1 Dec. 5, 2013

Related U.S. Application Data

(63) Continuation of application No. PCT/US2012/023741, filed on Feb. 3, 2012.

(60) Provisional application No. 61/439,596, filed on Feb. 4, 2011.

(51) Int. Cl.
| | |
|---|---|
| *G06T 7/00* | (2006.01) |
| *A61B 6/00* | (2006.01) |
| *A61B 8/00* | (2006.01) |
| *A61B 8/08* | (2006.01) |

(52) U.S. Cl.
CPC ........... *G06T 7/0012* (2013.01); *G06T 7/0083* (2013.01); *A61B 6/463* (2013.01); *A61B 6/5217* (2013.01); *A61B 8/463* (2013.01); *A61B 8/5223* (2013.01); *G06T 2207/10072* (2013.01); *G06T 2207/10116* (2013.01); *G06T 2207/10132* (2013.01); *G06T 2207/20136* (2013.01); *G06T 2207/20156* (2013.01); *G06T 2207/30021* (2013.01); *G06T 2207/30172* (2013.01)

(58) Field of Classification Search
None
See application file for complete search history.

(56) References Cited

U.S. PATENT DOCUMENTS

| | | | |
|---|---|---|---|
| 4,731,863 A | | 3/1988 | Schaetzing |
| 5,289,373 A | * | 2/1994 | Zarge ................... G06T 7/2033 382/128 |

(Continued)

OTHER PUBLICATIONS

Z Huo, S Li, M Chen, and J Wandtke, "Computer-aided interpretation of ICU portable chest images: automated detection of endotracheal tubes", Proc. SPIE, vol. 6915, 69152J, Mar. 17, 2008.*

(Continued)

*Primary Examiner* — Matthew Bella
*Assistant Examiner* — Soo Shin
(74) *Attorney, Agent, or Firm* — O'Banion & Ritchey LLP; John P. O'Banion

(57) ABSTRACT

A computer aided detection (CAD) method and system is configured to input chest radiographs and generate overlay layer for labeling and tracing tubes detected within the image. The input image is first preprocessed and then segmented according to anatomy. Seeds are generated from the segmented image and then used to grow the region. Tubes are selected from the grown region and data is overlayed on the image based on the grown seed path.

24 Claims, 22 Drawing Sheets

(56) References Cited

U.S. PATENT DOCUMENTS

| | | | |
|---|---|---|---|
| 5,341,439 A | 8/1994 | Hsu | |
| 5,830,141 A | 11/1998 | Cohen-Solal | |
| 5,872,859 A | 2/1999 | Gur | |
| 5,872,861 A * | 2/1999 | Makram-Ebeid | G06T 7/0012 128/922 |
| 5,930,329 A | 7/1999 | Navab | |
| 5,974,881 A | 11/1999 | Donskoy | |
| 6,067,373 A | 5/2000 | Doi | |
| 6,104,981 A | 8/2000 | Lechervy | |
| 6,134,966 A | 10/2000 | Donskoy | |
| 6,278,793 B1 | 8/2001 | Gur | |
| 6,366,684 B1 | 4/2002 | Gerard | |
| 6,373,918 B1 | 4/2002 | Wiemker | |
| 6,415,666 B1 | 7/2002 | Donskoy | |
| 6,542,628 B1 | 4/2003 | Muller | |
| 6,571,004 B1 | 5/2003 | Florent et al. | |
| 6,597,762 B1 | 7/2003 | Ferrant | |
| 6,748,257 B2 | 6/2004 | Ozaki | |
| 6,754,376 B1 * | 6/2004 | Turek | G06T 7/0012 382/131 |
| 6,760,468 B1 | 7/2004 | Yeh et al. | |
| 7,792,342 B2 * | 9/2010 | Barbu | A61B 6/12 382/128 |
| 2002/0072665 A1 | 6/2002 | Ozaki | |
| 2002/0106118 A1 * | 8/2002 | Ozaki | G06T 7/0083 382/132 |
| 2003/0053697 A1 * | 3/2003 | Aylward | G06T 7/0012 382/203 |
| 2003/0165262 A1 | 9/2003 | Jiang | |
| 2003/0167001 A1 | 9/2003 | Allain | |
| 2003/0174889 A1 | 9/2003 | Comaniciu | |
| 2004/0019447 A1 * | 1/2004 | Shachar | A61B 5/06 702/115 |
| 2004/0024292 A1 | 2/2004 | Heffernan | |
| 2004/0086161 A1 | 5/2004 | Birbeck | |
| 2004/0234133 A1 | 11/2004 | Bohm | |
| 2005/0100208 A1 | 5/2005 | Suzuki | |
| 2005/0129317 A1 | 6/2005 | Dalal | |
| 2005/0171409 A1 | 8/2005 | Arimura | |
| 2008/0050000 A1 | 2/2008 | Blaffert et al. | |
| 2008/0137923 A1 | 6/2008 | Spahn | |
| 2010/0296718 A1 * | 11/2010 | Ostrovsky-Berman | G06T 7/602 382/133 |

OTHER PUBLICATIONS

BM Keller, AP Reeves, MD Cham, CI Henschke, and DF Yankelevitz, "Semi-Automated Location Identification of Catheters in Digital Chest Radiographs," Medical Imaging 2007: Computer-Aided Diagnosis, Proc. of SPIE vol. 6514, 65141O.*
O Friman, M Hindennach, C Kuhnel, and H-O Peitgen, "Multiple hypothesis template tracking of small 3D vessel structures," Medical Image Analysis, vol. 14, 2010, pp. 160-171.*
M Hoffmann, et al. "Semi-Automatic Catheter Reconstruction from Two Views," N. Ayache et al. (Eds.): MICCAI 2012, Part II, LNCS 7511, pp. 584-591, 2012.*
Korean Intellectual Property Office, International Search Report and Written Opinion issued on Jul. 27, 2012 for corresponding International Patent Application No. PCT/US2012/023741 (pp. 1-8) and claims searched (pp. 9-15) pp. 1-15.
Brad M. Keller, et al., "Semi-automated location identification of catheters in digital chest radiographs", SPIE Medical Imaging 2007, vol. 6514, pp. 1-9.
Chen Sheng and Li Li, Wang Pei, "Automatic detection of supporting device positioning in intensive care unit radiography", The International Journal of Medical Robotics and Computer Assisted Surgery, vol. 5, No. 3, pp. 332-340, (2009).

* cited by examiner

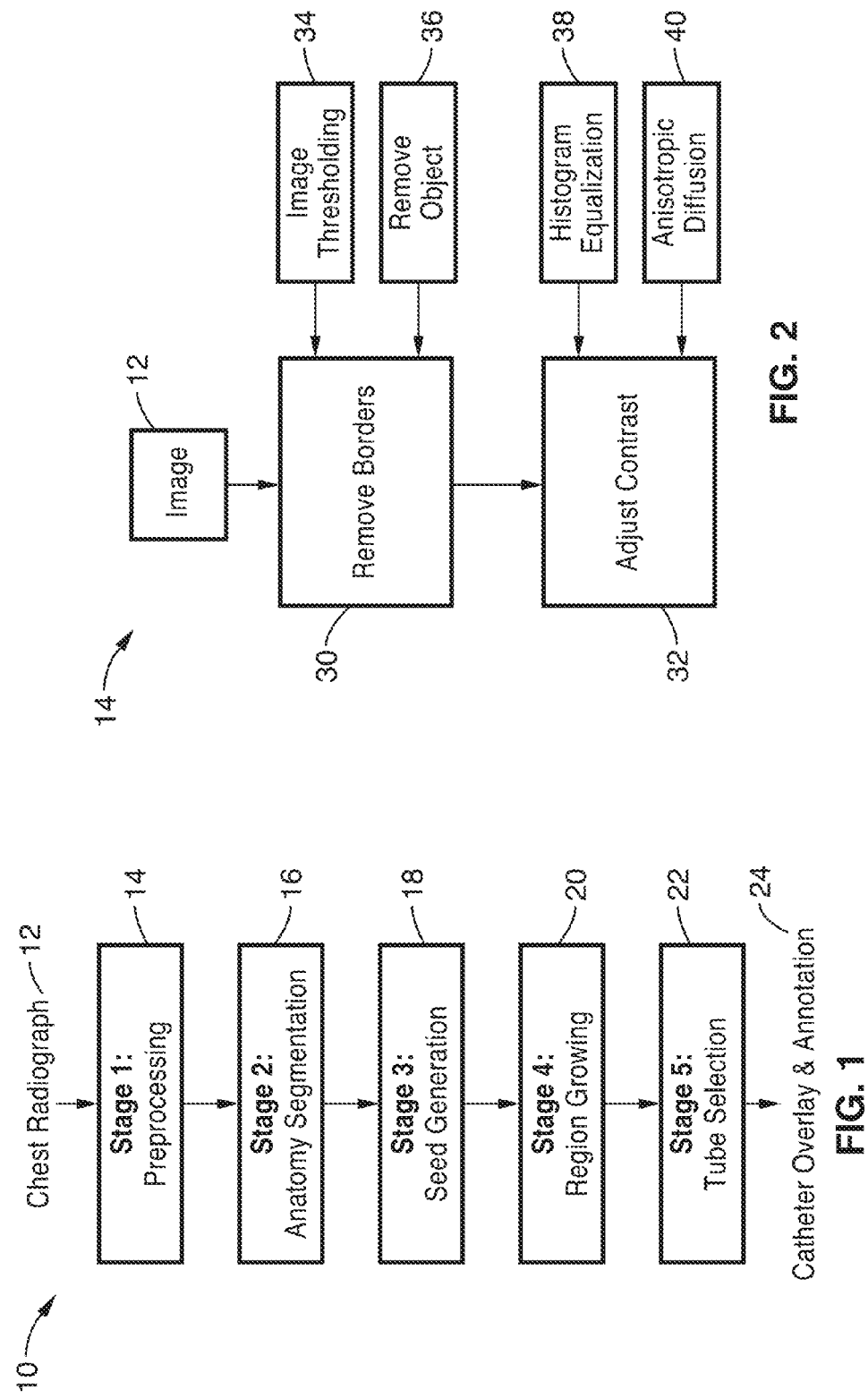

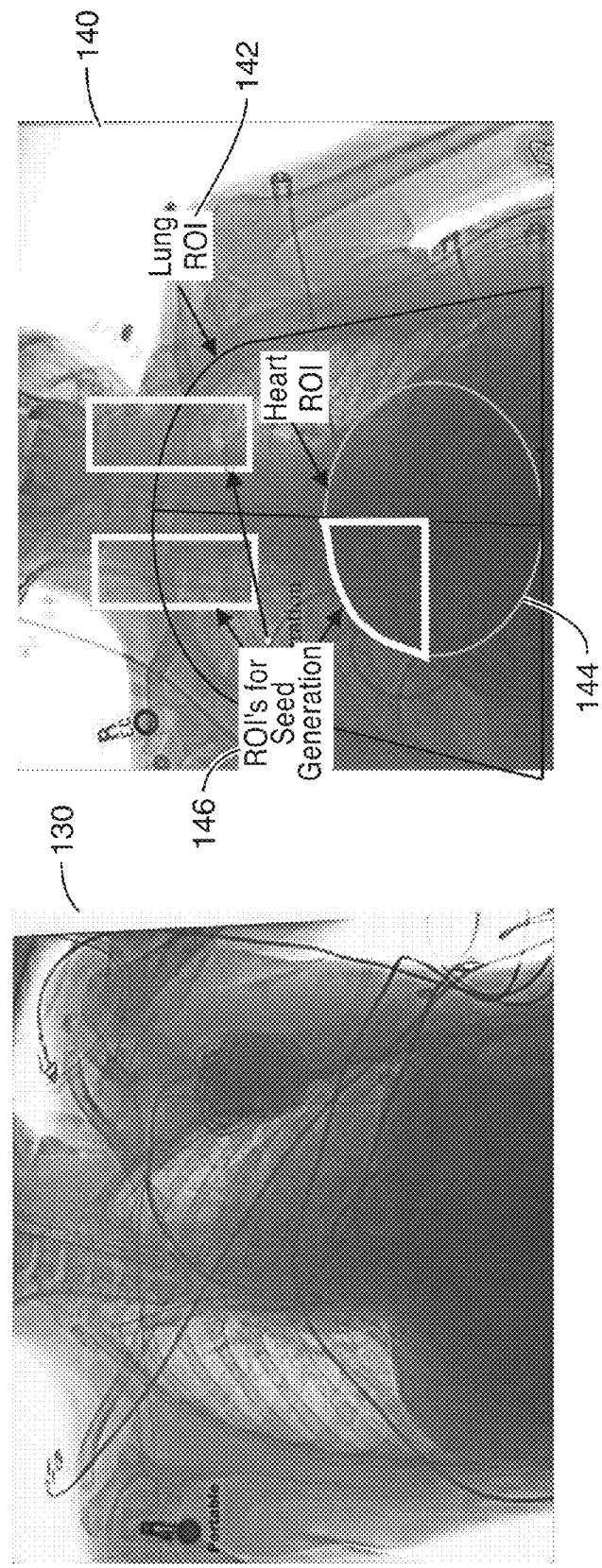

METHODS AND APPARATUS FOR COMPUTER-AIDED RADIOLOGICAL DETECTION AND IMAGING

CROSS-REFERENCE TO RELATED APPLICATIONS

This application is a 35 U.S.C. §111(a) continuation of PCT international application number PCT/US2012/023741 filed on Feb. 3, 2012, incorporated herein by reference in its entirety, which is a nonprovisional of U.S. provisional patent application Ser. No. 61/439,596 filed on Feb. 4, 2011, incorporated herein by reference in its entirety. Priority is claimed to each of the foregoing applications.

The above-referenced PCT international application was published as PCT International Publication No. WO 2012/106580 on Aug. 9, 2012 and republished on Oct. 4, 2012, and is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally image detection, and more particularly to detection of man-made devices within the body of a patient.

2. Description of Related Art

Numerous systems have been developed for recognizing man-made devices (buildings, planes, cars, etc) in non-medical images (digital photographs, satellite images, etc). While computer-aided detection (CAD) systems have been developed for detecting and measuring organs and diseases in medical images, CAD has been traditionally only designed for oncology tasks to aid physicians in identifying subtle nodules, lesions etc. However CAD holds much promise in aiding radiologists in routine clinical tasks.

Currently, the presence and location of implantable man-made devices (IMD's) in medical images are assessed visually by a radiologist. The use of computer aided detection would substantially reduce the cost of this frequently performed radiologic interpretation.

Chest radiographs are used to confirm placement of life support tubes in patients, and incorrect placement of these tube can cause severe complications and can even be fatal. Incorrect placements of the Endotracheal (ET) tube typically include the tube being placed in the esophagus or in the soft tissue of the neck. Incorrect placement of the Nasogastric (NG) tube, for example, in the pleural cavity can cause pneumothorax. Accordingly, detecting tube placement is critical for patients in ICU's as incorrect tube placements can cause serious complications and can even be life threatening.

Assessing tube placement on chest radiographs is a difficult, time consuming task for radiologists and ICU personnel given the high volume of cases and the need for rapid interpretation. Chest radiographs are the quickest and safest method to check placement of these tubes. Tertiary ICU's typically generate hundreds of chest radiographs per day to confirm tube placement in patients. Radiographs of patients in ICU's are often cluttered with different tubes providing life support and wires monitoring the patient vital signs some outside and some inside the body. This makes the task of identifying these tubes a difficult and time consuming process for radiologists.

There has been very little research on detecting catheters, tubes and wires in chest radiographs, despite the significant clinical need.

Accordingly, an objective of the present invention is a system and methods to automatically detect and classify catheters with minimal change to the radiology workflow.

BRIEF SUMMARY OF THE INVENTION

The methods and systems of the present invention comprise a fully automatic CAD system designed to detect and classify man-made devices (IMD's), and in particular catheters on chest radiographs, using a robust voting algorithm-based approach.

The CAD systems of the present invention are configured to detect and classify catheters on radiographic images containing multiple tubes in close proximity.

The systems and methods of the present invention are configured for detection and surveillance of IMD's on a large number of images, preventing what would normally be a time-consuming and challenging task for physicians, and minimizing healthcare costs. This computer-aided detection system of the present invention reduces time and costs and increase accuracy, consistency and level of detail of interpretation. It is also configured to detect critical device failures that put patient safety at risk.

The CAD system and methods of the present invention may also detect changes in position of an IMD between serial images. This may be achieved using image registration to align serial images of a given patient. The distances between corresponding pixels classified as IMD in the registered images are measured.

An aspect of the invention is a computer automated detection method for detection of one or more implantable man-made devices (IMD's) within the body of a patient. The method includes the steps of: receiving an image of the patient; segmenting the image into one or more regions of interest, the regions of interest corresponding to anatomical features of the patient; generating one or more seed points from a designated region of interest from the one or more regions of interest in the segmented image; projecting one or more grown seed points along a path based on the one or more generated seeds; and overlaying an IMD position based on the grown seed path over the patient image.

The CAD system and methods of the present invention were tested to show feasibility of automatic detection of both ET tube and NG tube on chest radiographs, with the potential to increase radiologist productivity and confidence, and to improve patient safety.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 shows a flow diagram of a computer aided detection (CAD) method for catheter detection and classification.

FIG. 2 shows a flow diagram for a preprocessing method associated with the method of FIG. 1.

FIG. 10 shows the chest radiograph of FIG. 9AB after pre-processing in accordance with the present invention.

FIG. 11 shows the pre-processed image of FIG. 10 with anatomical segmentation for CVC detection.

DETAILED DESCRIPTION OF THE INVENTION

Figure 3B:
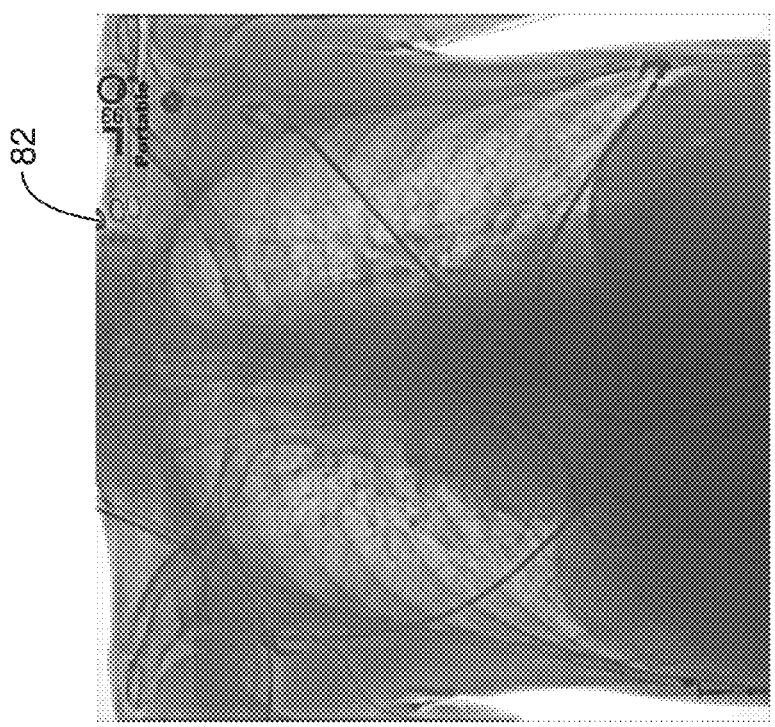
FIG. 3B shows the chest radiograph of FIG. 3A after pre-processing in accordance with the present invention.

The present invention includes systems and methods including a computer vision system to automatically detect and assess implantable, man-made devices (IMD's) in medical images. The system and methods of the present invention are configured for detecting devices such as, but not limited to, pacemakers, pumps, stents, plates, coils, tubes, catheters, clips, nails, screws, microchips, etc.

The medical imaging modalities for use in the systems and methods of the present invention may in include, but are not limited to, X-ray, MRI, ultrasound, nuclear, optical. The CAD system of the present invention is configured for automatically determining one or more IMD attributes: location, category, manufacturer and characteristics; comparison to manufacturer's specifications; movement between serial images; safety verification and recall.

In a preferred embodiment, the system and methods of the present invention take one or more medical images as input and automatically generate/output an IMD report containing this information.

By way of example, and not of limitation, the CAD system and methods of the present invention use image feature extraction and pattern classification methods (mathematical models) to automatically detect and classify IMDs in medical images.

In a preferred embodiment, the CAD system and methods of the present invention are configured for aiding radiologists in detecting tubes in ICU patients. The two most often used catheters especially in the ICU's are the Endotracheal (ET) and the Nasogastric (NG) tube. The endotracheal tube is placed to aid the patient in breathing and to keep the trachea open and at times it is also used to administer drugs. The tip of the endotracheal tube is placed about 5 cm above the carina. The nasogastric tube is primarily used for feeding and for administering drugs. It can also be used to drain the contents of the stomach which may be necessary in case of poisoning or in preparation for surgery.

Referring to FIG. 1, the CAD method 10 of the present invention is configured to input chest radiographs 12 (e.g. from bed-side ICU portable x-ray stations), and generates the annotation or overlay layer 24 for labeling and tracing tubes. The CAD system 10 comprises of five primary steps. First, the chest radiographs are preprocessed at step 14. The preprocessed image is then segmented according to anatomy at step 16. Seeds are generated from the segmented image at seed generation step 18. The seeds from step 18 are then used to grow the candidate tube regions at step 20. Tubes are then selected at step 22.

It is appreciated that the method 10 shown in FIG. 1 may also comprise a programming application (e.g. application programming 320 shown in FIG. 20) containing individual modules 12, 14, 16, 18, 20, and 22 for carrying out the methods of the present invention on a computer/processor or the like. Each of the individual steps/modules are described in further detail below for detection and classification of NG and ET tubes, as well as CVC's (center venous catheter) individually.

Referring now to FIG. 2, pre-processing method 14 is configured at step 30 to remove borders in the radiographic image 12. As shown in FIG. 3A, bedside chest radiographs 80 usually contain borders 84 that should be removed before further processing. This is accomplished by thresholding the image at step 34 based on the mean intensity of the entire image 80, followed by connected component analysis 36 to remove the object with the greatest area.

After the removal of borders at step 30, the image 12 is enhanced by using contrast adjustment step 32. Contrast adjustment step 32 may comprise histogram equalization step 38 (e.g. CLAHE (Contrast Limited Adaptive Histogram Equalization)), which enhances the regions of low contrast.

Furthermore, and anisotropic diffusion 40 may be used to further enhance the image 12 while preserving tube/catheter edges.

Figure 3A:
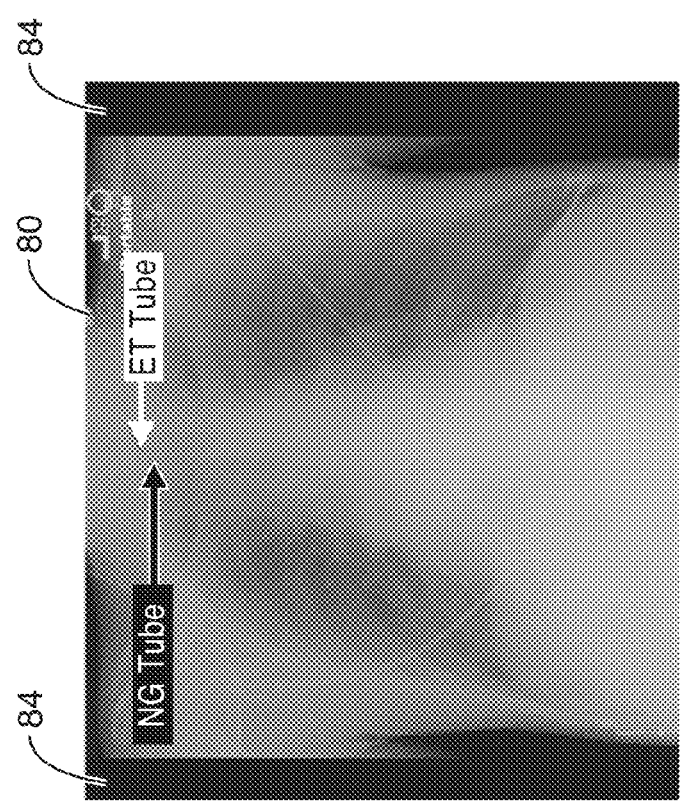
FIG. 3A illustrates a chest radiograph with ET, NG tubes prior to pre-processing.

FIG. 3B shows the chest radiograph 82 after pre-processing step 14 in accordance with the present invention.

Figure 4:
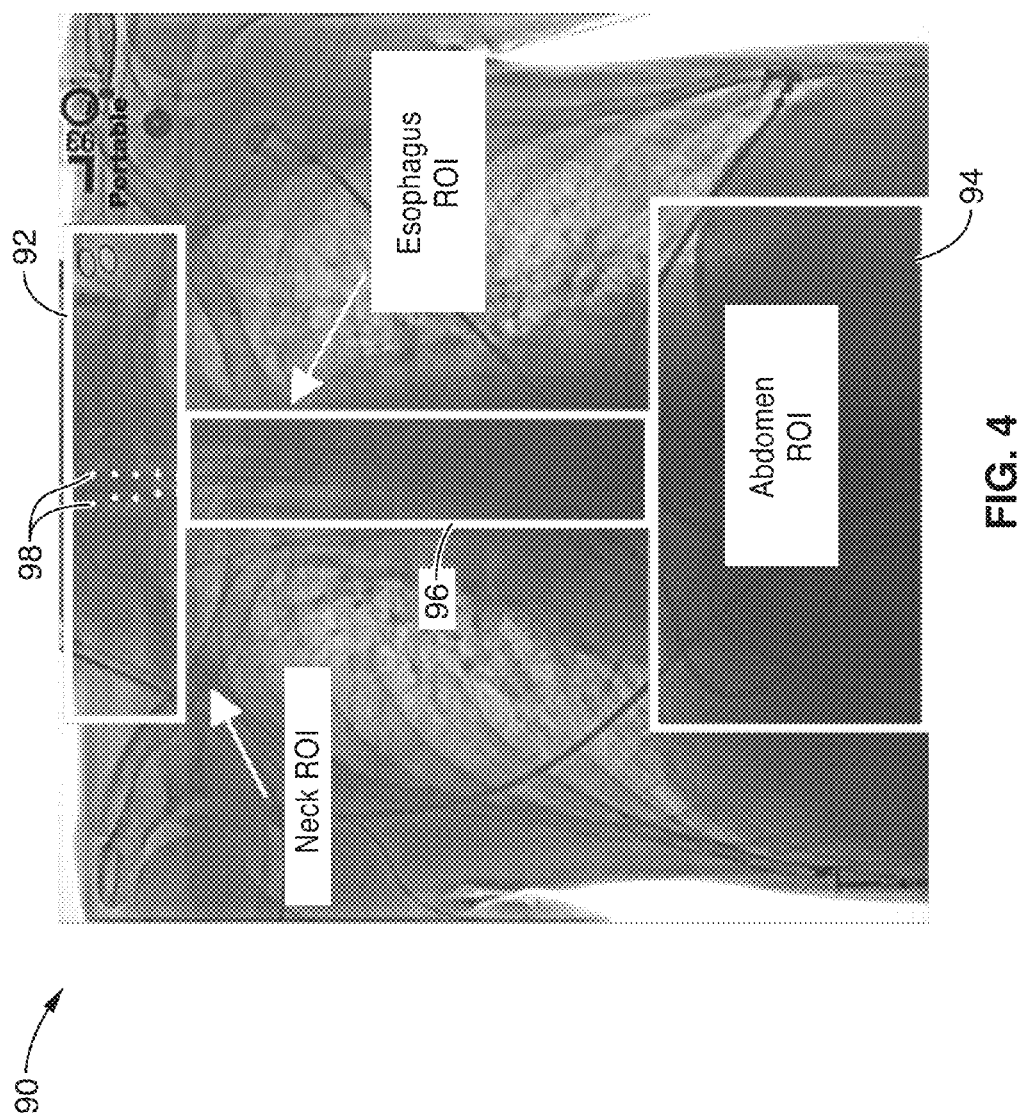
FIG. 4 shows the pre-processed image of FIG. 3B with anatomical segmentation and generated seeds in accordance with the present invention.

After the image is preprocessed at step 14, the image is then segmented at step 16. FIG. 4 shows the pre-processed image of FIG. 3B with anatomical segmentation and generated seeds 90.

Identifying approximate anatomy location is useful in both seed generation and eliminating false positives. Approximate bounding boxes are computed for each anatomical region of interest using template matching. For example, rectangular templates for a neck bounding box 92, esophagus bounding box 96, and abdomen bounding box 94 are generated. Relative positions of the bounding boxes are taken into account to optimize the placement of the bounding boxes.

Figure 5:
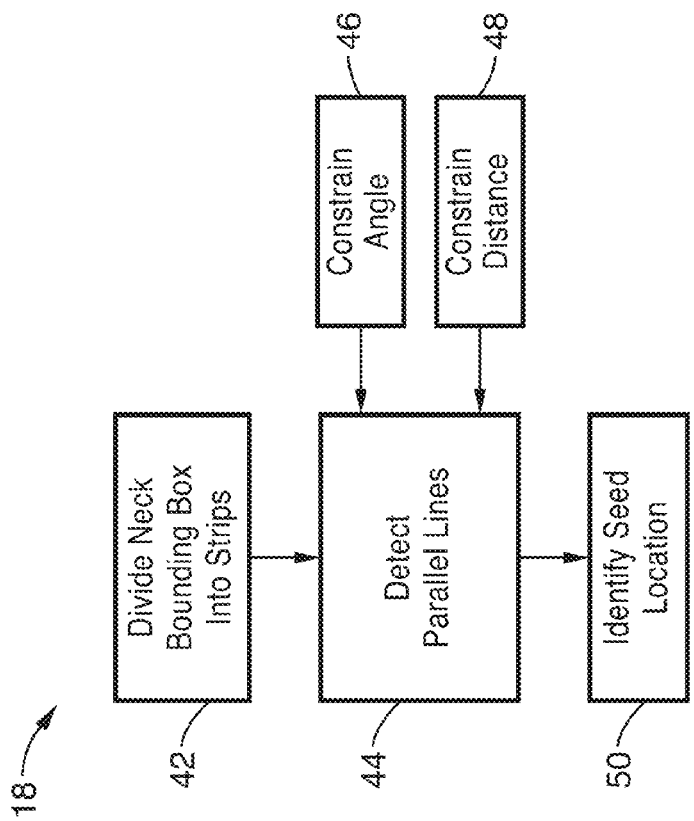
FIG. 5 illustrates a flow diagram of a seed generation method in association with the method of FIG. 1.

Referring now to FIG. 5, which show seed generation step 18 in more detail, multiple seeds 98 (see FIG. 4) are generated in the neck ROI 92 to be used for region growing. The neck ROI 92 provides a good starting point, as this location is common for both the NT and NG tubes (which are placed into the patient's body through the patient's mouth) and is generally well presented in radiographs. This is accomplished by dividing the neck ROI 92 into strips 42 and identifying parallel lines on the gradient image at step 44. A Hough transform-based parallel lines detector may be used to find the lines by constraining the perpendicular distance 48 between lines and orientation/angle 46 as parameters. Once the parallel lines have been identified, the seed 98 location is calculated at step 50 as the mid-point between the parallel lines. Seeds 90 may be generated by using both the ET Tube and NG Tube profiles. However, the generated seeds are not labeled as ET seeds or NG seeds.

The parallel lines detection step 44 is run within each strip within the bounding box 92. One seed point 98 is generated from each pair of parallel lines detected in a strip. This process will thus potentially generate multiple seed points. The orientation parameter 46 is with respect to the image 90 coordinate frame. Generally, only lines that are close to vertical within the image are used.

Figure 6:
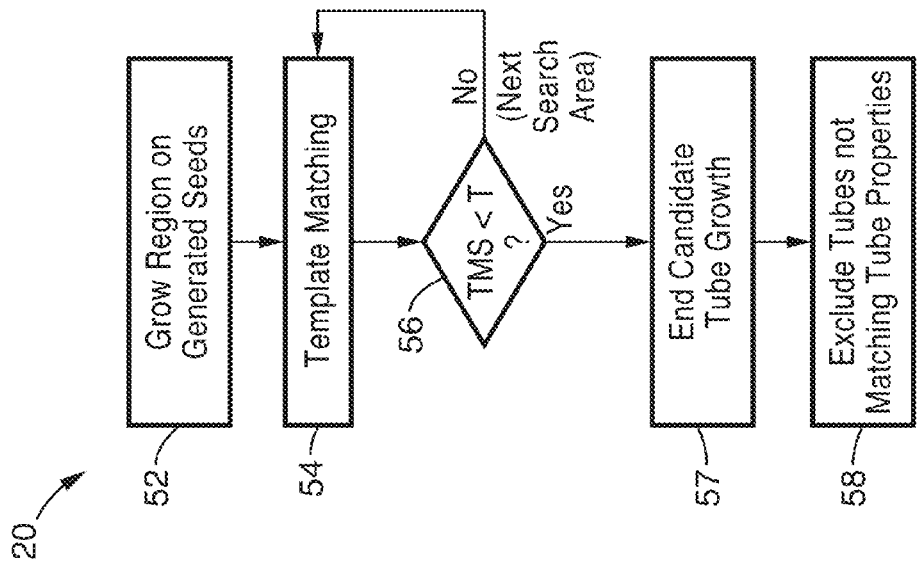
FIG. 6 shows a flow diagram of a region growing method in association with the method of FIG. 1.

FIG. 6 shows a flow diagram of a region growing method 20 in greater detail. Region growing step 20 is carried out on all the generated seeds 98 from the previous stage using template matching 54. For example, the seeds 98 are grown or projected at step 52 from the neck ROI 92 and into other ROI's. The templates are designed as a function of the tube profile. For example, if a particular tube is known by the physician/radiologist, then that tube is selected from a group of preformed templates having tube dimensional and orientation parameters. Template matching 54 accepts orientation, translation and stored tube profiles as parameters, and returns matched orientation and translation. After each generated growth of the tube, a template matching score is calculated at step 56. Region growing is stopped if the template match score (TMS) is continuously below a given threshold T. The template match score corresponds to the confidence that a new point lies within the expected path and orientation of the previous seed points 98. Consecutive low template match scores correspond to the likelihood that the end of the tube is reached. If the TMS is above threshold T, than the module 20 continues to template match at step 54. If the TMS is below threshold T, than the module 20 stops candidate growth step 57.

At step 58, generated tubes are excluded if they do not meet the length and location properties of the particular tube (e.g. tube parameters stored in the tube profile). The ET tube location is limited to the neck 92 and esophagus 96 ROI's and NG tube location is limited to the neck 92, esophagus 96 and abdomen 94 ROI's.

Figure 7:
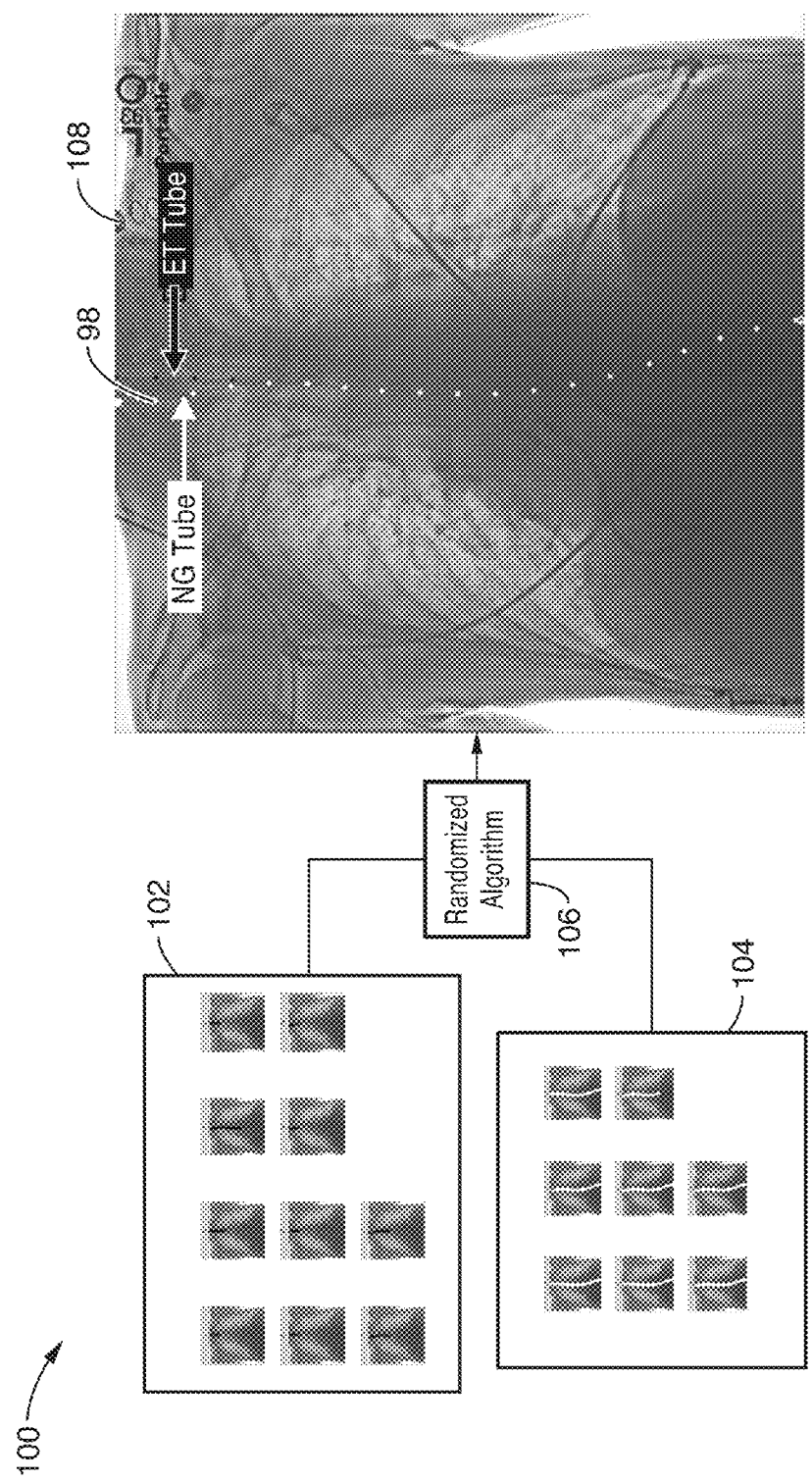
FIG. 7 shows images used for the region growing and tube selection steps of the present invention.

FIG. 7 shows images 100 used for the region growing 20 and tube selection steps 22 of the present invention. The translation parameter for template matching 54 is relative to the last tube point detected (last place the template was matched) during the growing step 20. The orientation of the template is based on the orientation of the previously matched template (since the orientation is expected to change smoothly as you grow along the tube).

The group of thumbnail images 102 shows growths (tube candidates) from multiple seeds for ET tube growth. The group of thumbnail images 104 shows growths (tube candidates) from multiple seeds for NG tube growth.

The image groups 102 and 104 are processed through the voting scheme 106 used in tube selection 22 to generate the final CAD output image 108 with grown seed points 98.

Figure 8:
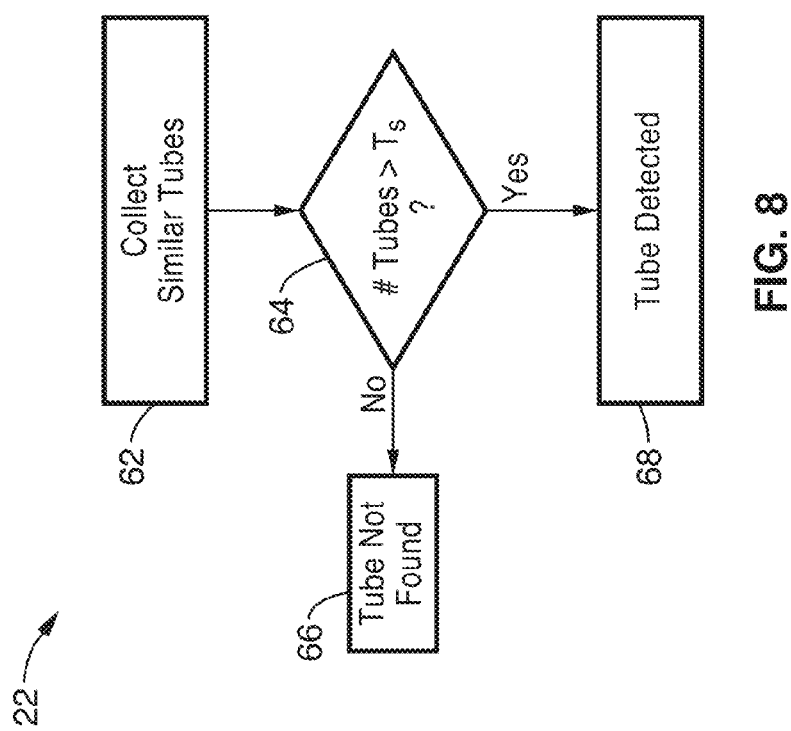
FIG. 8 shows a flow diagram of a tube selection (voting) method in association with the method of FIG. 1.

FIG. 8 shows a flow diagram of a tube selection method 22. The pairwise correspondence between seed growths (candidate tubes) are computed via voting scheme algorithm 106 using distance maps. This allows candidate tubes with similar locations to be clustered into groups at step 62. Tubes segmented via region growing step 20 are grouped based on tube type. An intra-comparison is performed to identify similar tubes with respect to location.

The number of tube candidates within the group determines the confidence for that tube cluster. The more tubes found, the more confidence there is that the tube is correct. A confidence threshold $T_s$ is applied at step 64 to determine whether a tube is found with sufficient confidence and is displayed. If the number of tubes exceeds the confidence threshold $T_s$, then a tube is deemed detected at step 68. If no tube clusters from the region growing exceed the confidence threshold $T_s$, then a result of "tube not found" is returned at 66. The system 10 may be configured to still show an estimated tube position (of low confidence) based only on the seed points.

Figure 9B:
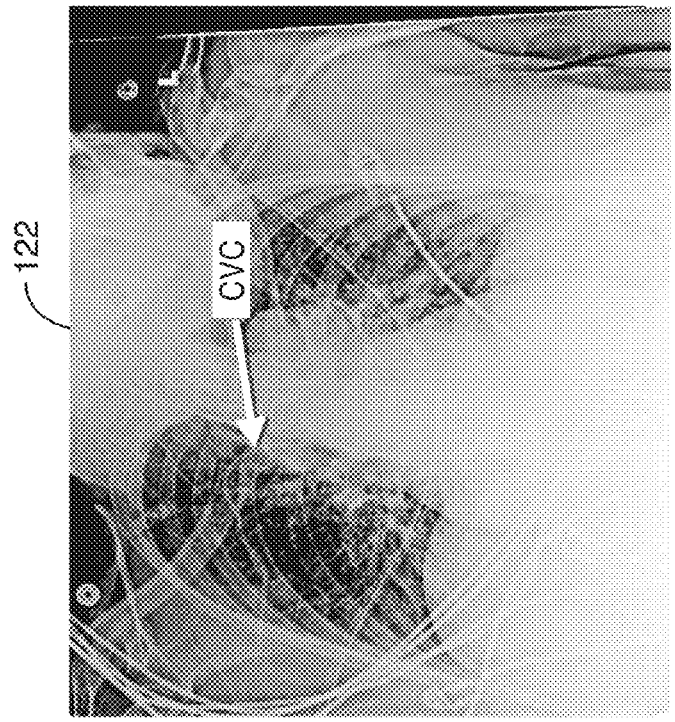
FIGS. 9A and 9B illustrate a chest radiographs with CVC tube prior to pre-processing.
Figure 9A:
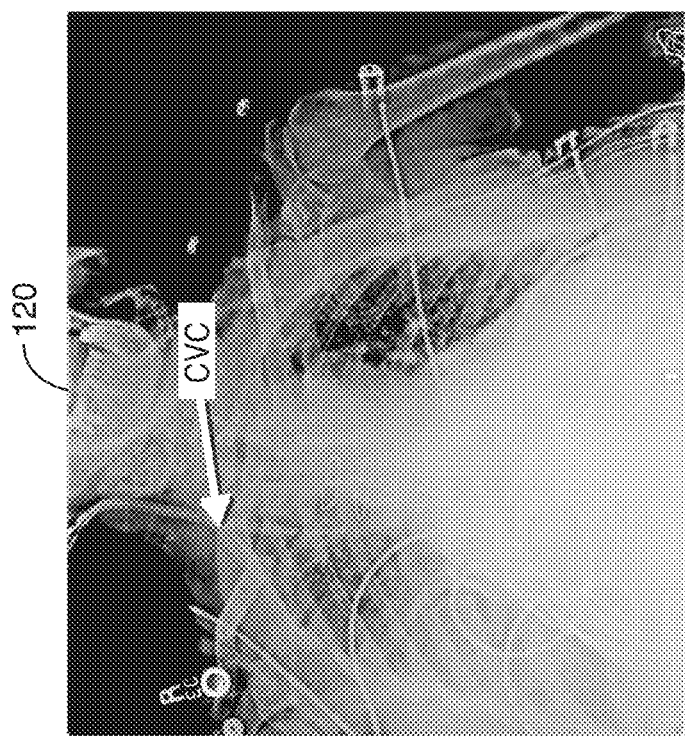

The steps in method 10 may also be applied for CVC centerline detection. FIGS. 9A and 9B illustrate chest radiographs 120 and 122 with CVC tube prior to pre-processing. FIG. 10 shows the chest radiograph 130 after pre-processing step 14 for a CVC based radiograph.

Referring now to FIG. 11, the anatomy segmentation step 16 is limited to identifying both the lung 142 and heart 144 ROI's, this is achieved by using a shape model based approach. FIG. 11 shows the pre-processed image 140 with anatomical segmentation for CVC detection. The shape model is generally trained offline on pre-segmented lung 142 and heart 144 ROI's. The shape model captures the shape statistics and the boundary intensity/texture profile statistics of the lung field and the heart fields. Given an input image the trained shape model identifies the lung ROI's 142 automatically. The ROI's for seed generation 146 are defined relative to the segmented lung 142 and heart 144 ROI's. Patient position may also be estimated, and corrected if necessary (See images 120 and 122 in FIGS. 9A and 9B.

Figure 12:
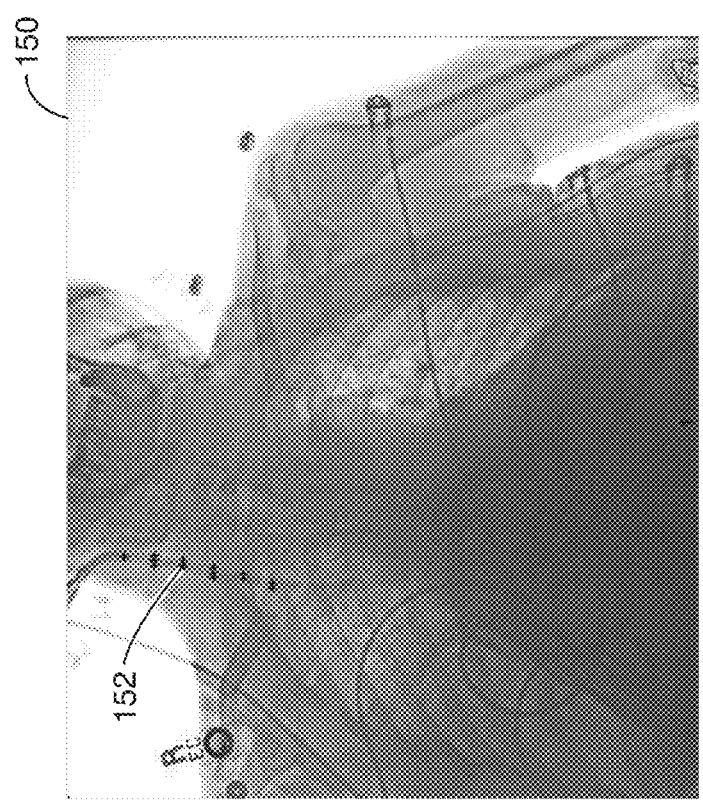
FIG. 12 illustrates an image showing CVC seed generation.

FIG. 12 illustrates an image 150 showing CVC seed generation. For CVC seed generation, method step 18 first starts from the interior of heart ROI 144, and moves outward towards the right lung ROI 142. Multiple seeds 152 are generated in both the ROI's 146 to be used for region growing. This is accomplished by dividing the ROI into strips (e.g. at block 42 in FIG. 5 and identifying parallel lines (step 44) on the gradient image. Once the parallel lines have been identified the seed location is taken as the mid-point between the parallel lines at step 50. The Hough transform based parallel lines detector accepts the perpendicular distance between lines 48 and orientation 46 as parameters. Seeds are generated by using both the input CVC tube profiles as parameters 46/48, and the orientation is limited to being close to perpendicular (e.g. vertical) for both the ROI's 146.

Figure 13:
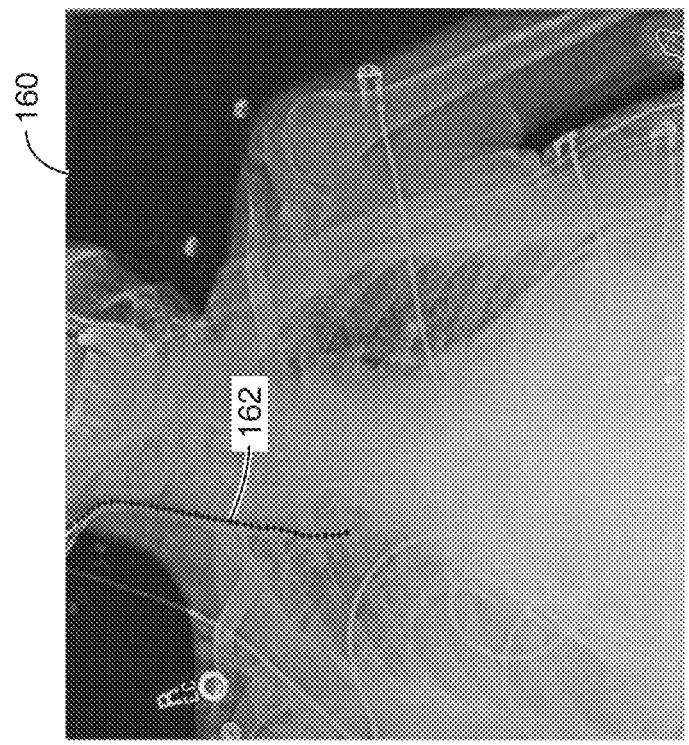
FIG. 13 illustrates an image showing CVC region growing and tube selection.

FIG. 13 illustrates an image 160 showing CVC region growing 162 and tube selection. Region growing step 20 is carried out on all the generated CVC seeds from step 18 using template matching, wherein the templates are generated as a function of a pre-determined CVC tube profile. Template matching step 54 accepts orientation, translation and tube profile as parameters and returns matched orientation and translation. Template based region growing 20 is limited to lung 142 and heart 144 ROI's.

At step 58, tubes are excluded if they do not meet predefined length and location properties for the CVC (e.g. length and curvature, catheter end-point location and catheter path). As a general rule, the CVC tube seeds 162 must terminate at the heart, e.g. heart ROI 144, and originate either from the arm or the neck.

For the NG, ET, and CVC detection methods, the display of the tube position as an overlay on the image (step 24) includes a "region of uncertainty" around the endpoint, and is calculated according to Eq. 1:

$$\overline{C} = \frac{1}{T}\sum_{t=S}^{E} C_t \qquad \text{Eq. 1}$$

where C is the confidence of each point on the tube, $C_t$ is the confidence at the $t^{th}$ point on the tube, t=1 to T, where T is the last point on the extracted tube including and beyond the end-point. S (parameter) corresponds to a start location for the computation of the region of uncertainty.

The region is centered at the detected location of the tube end point (E) and has a radius that is estimated from break point ($P_1$) and post point ($P_2$—possible detected tube point beyond the end point, following tube trajectory) according to Eq. 2:

$$P_1 = \min(\arg(C_t < k_1 \overline{C})), \text{ where } t \in [S,E], \text{ default } P_1 = E \qquad \text{Eq. 2}$$

where k is a constant, k∈[0,1].

In order to estimate point $P_2$, the tube is extended by region growing from point E along the trajectory until region growing ceases at T due to stopping rule 56 (FIG. 6) or due to anatomic ROI constraints, according to Eq. 3 and 4:

$$P_2 = \max(\arg(C_t > k_2 \overline{C})), \text{ where } t \in [E,T], \text{ default } P_2 = E \qquad \text{Eq. 3}$$

$$\text{radius} = \max(\|P_1 - E\|, \|P_2 - E\|) \qquad \text{Eq. 4}$$

Figure 14:
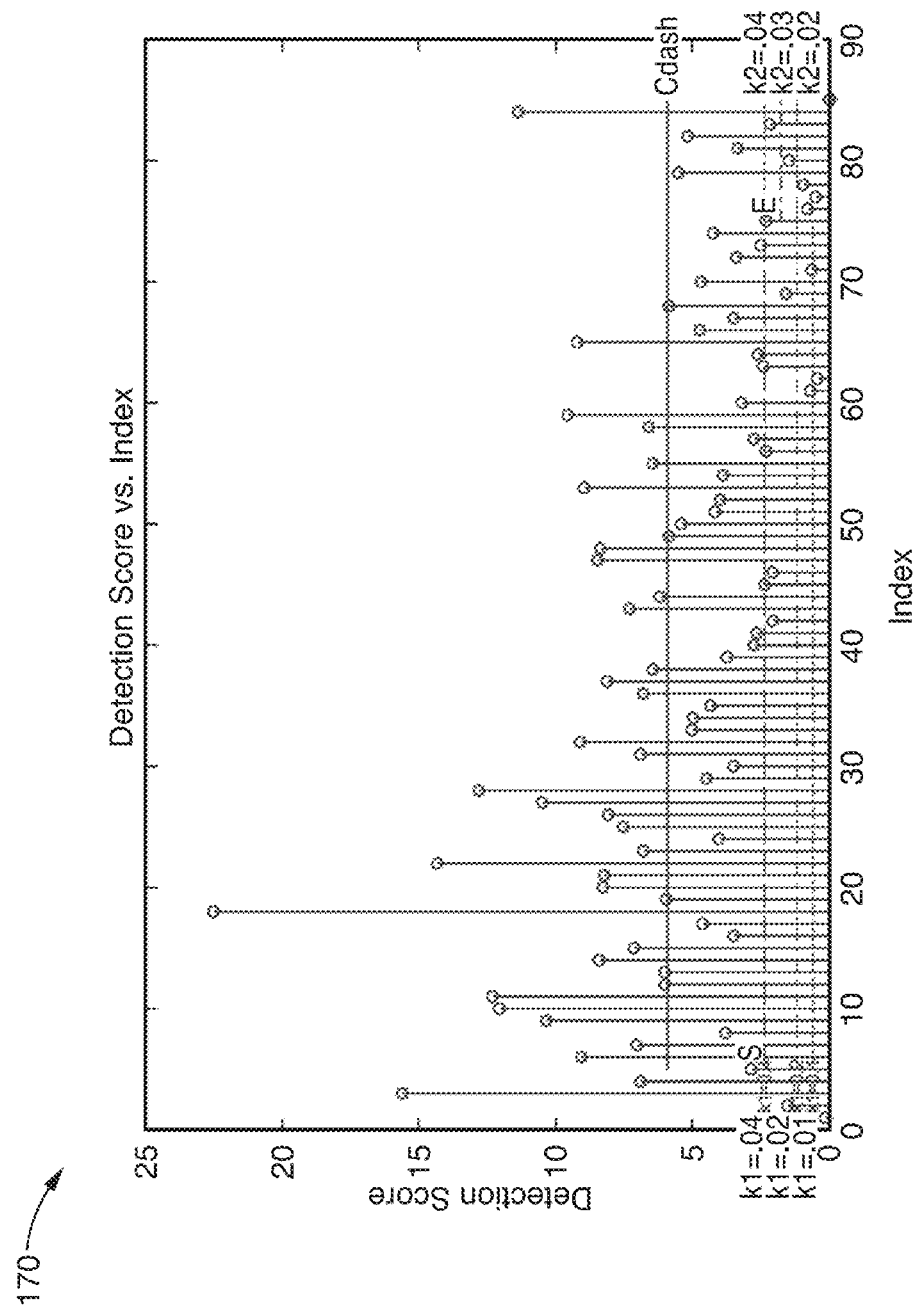
FIG. 14 shows a plot of detection scores for points along a NG tube path.
Figure 15:
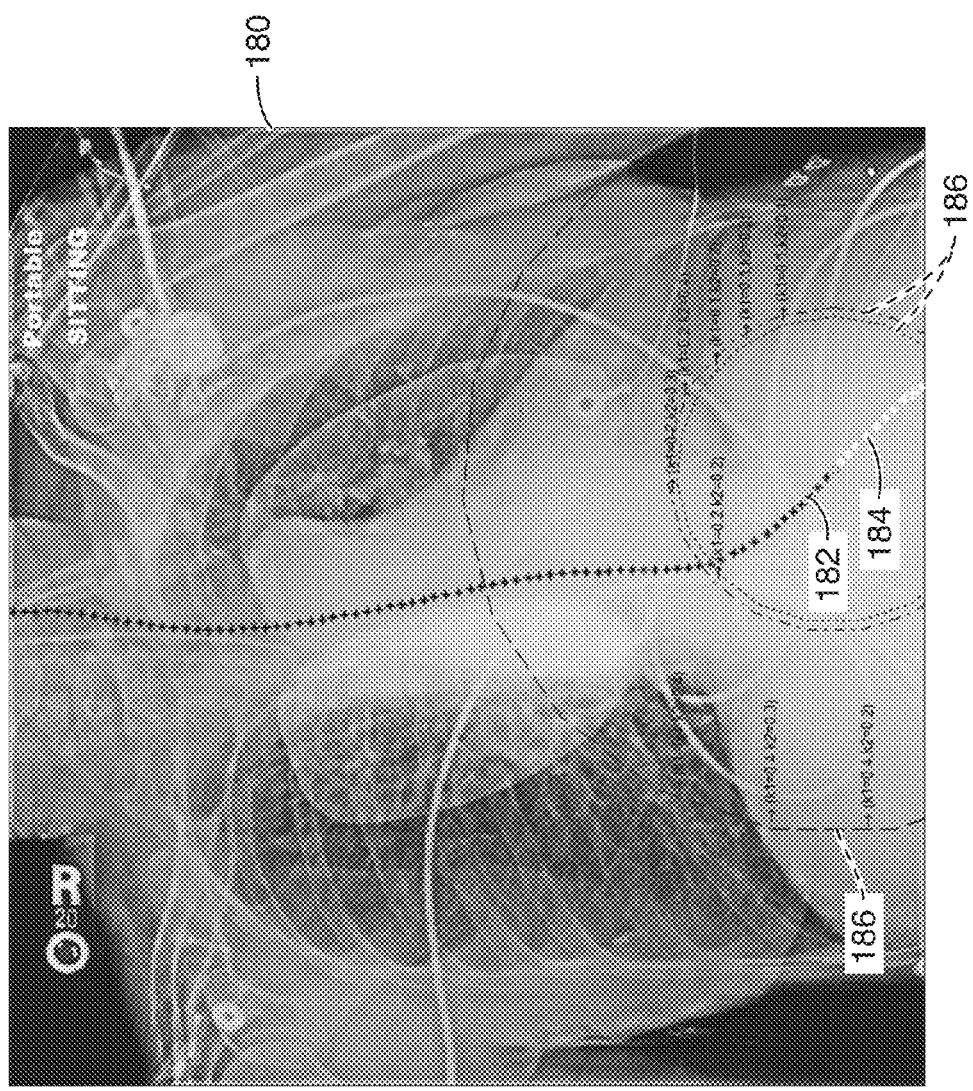
FIG. 15 is an image showing regions of uncertainty for various K1 and K2 values for the NG Tube.

FIG. 14 shows plot 170 of confidence $C_t$ vs. position t along the length of an NG tube, with lines representing the mean $C_t$ value and $kC_t$ for various values of k. The detected tube 182 and the resulting regions of uncertainty 184 for different k-values 186 are overlayed on the chest x-ray image 180 of FIG. 15.

Figure 16:
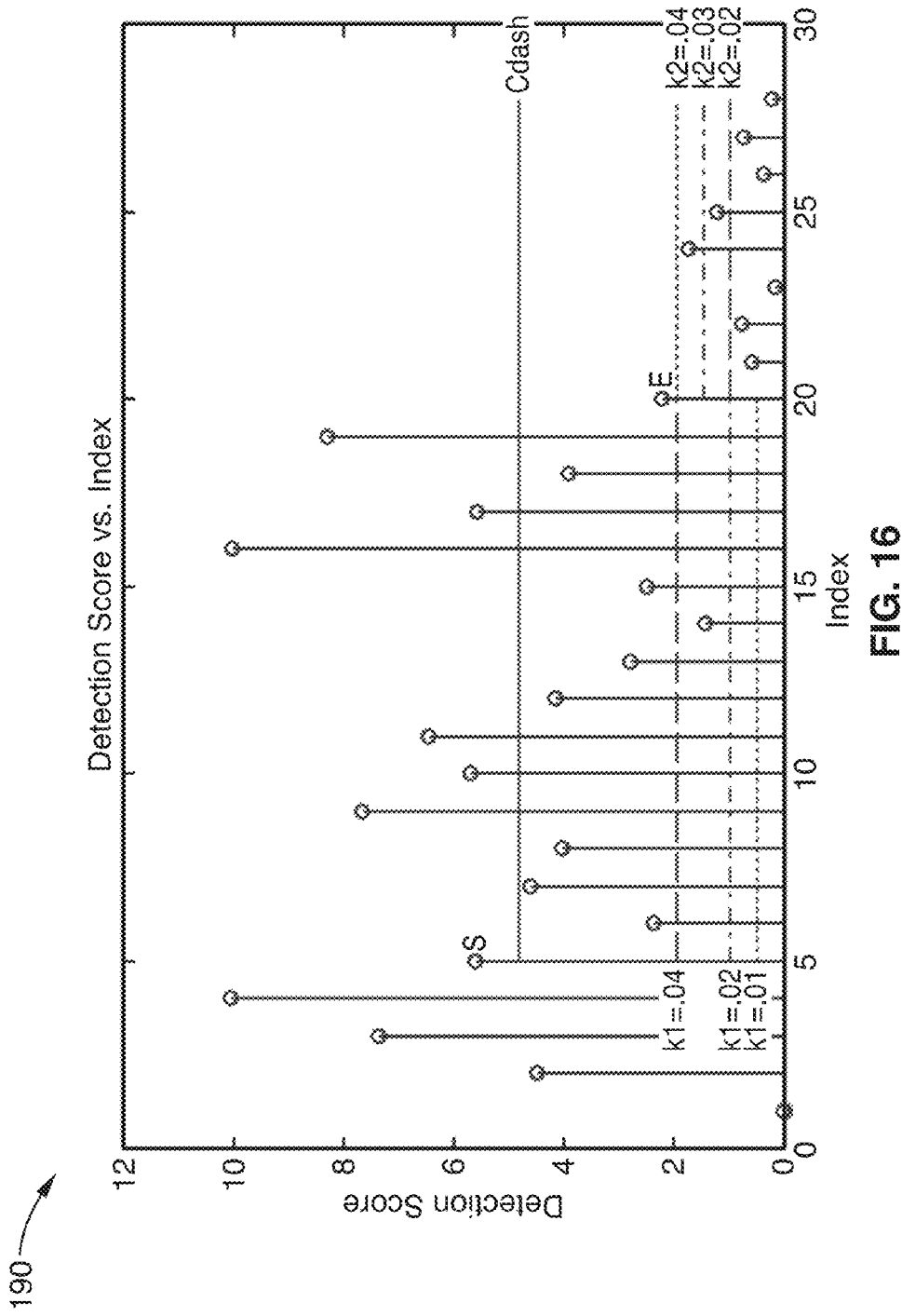
FIG. 16 shows a plot of detection scores for points along an ET tube path.
Figures 17A, 17B:
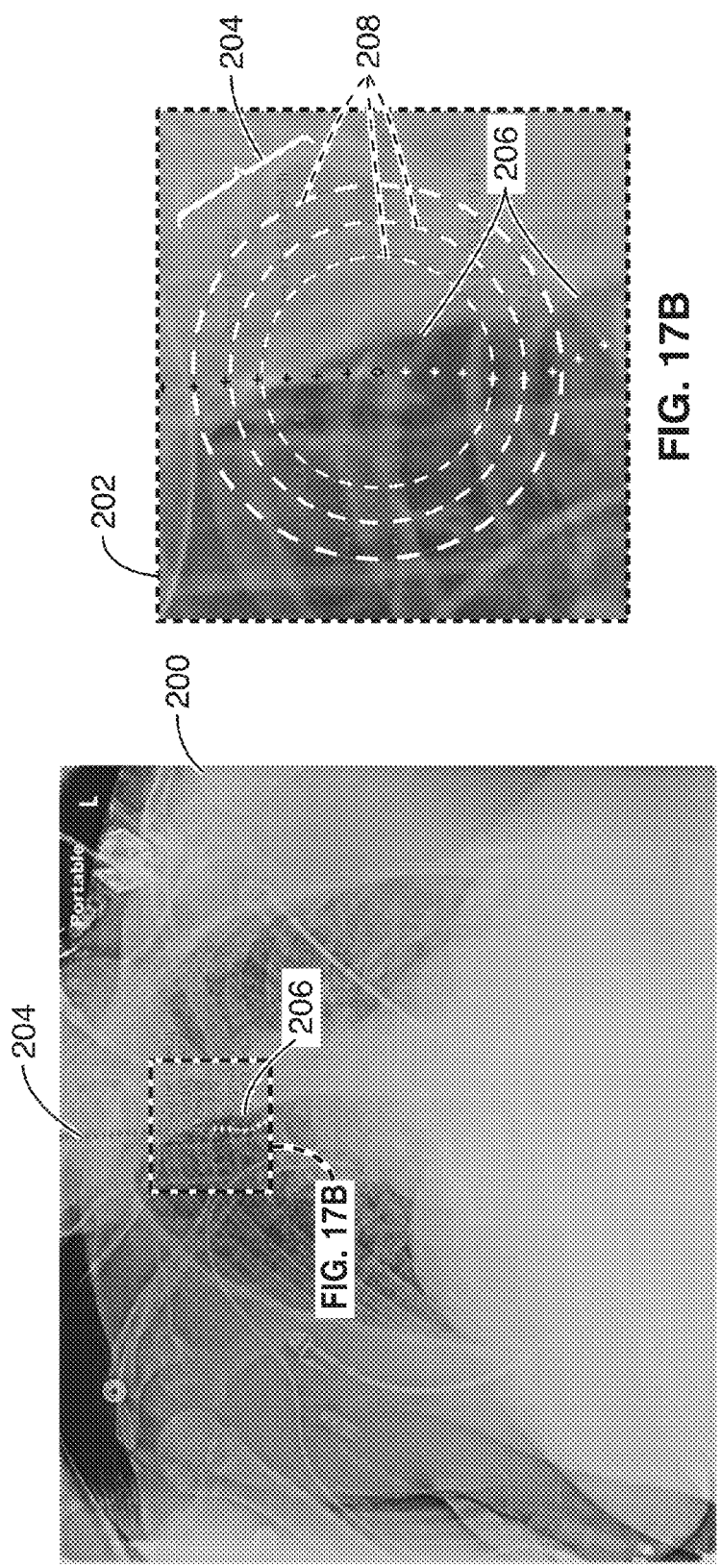
FIGS. 17A and 17B are images showing regions of uncertainty for various K1 and K2 values for the ET Tube.

FIGS. 16, and 17A and 17B show similar images for the ET tube. FIG. 16 shows plot 190 of confidence $C_t$ vs. position t along the length of an ET tube 190, with lines representing the mean $C_t$ value and $kC_t$ for various values of k. The detected tube 204 and the resulting regions of uncertainty 206 for different k-values 208 are overlayed on the chest x-ray image 200 of FIG. 17A and exploded view 202 of FIG. 17B.

Optimal constants $k_1$ and $k_2$ may be determined from a set of training x-ray images by plotting % detections (region encloses true end point) vs. sum of region areas (similar to an ROC analysis). The region may also be modified by anatomic constraints that limit where the tube end can be located given the detected portion.

Figure 18A:
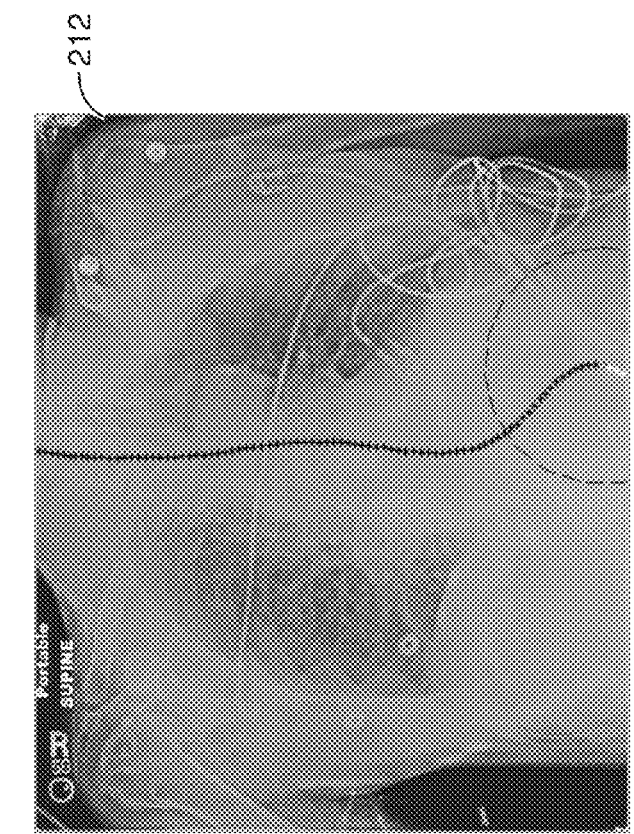
FIGS. 18A through 18C are images showing region of uncertainty results for K1=0.2 and K2=0.4 values for the NG Tube.
Figure 18B:
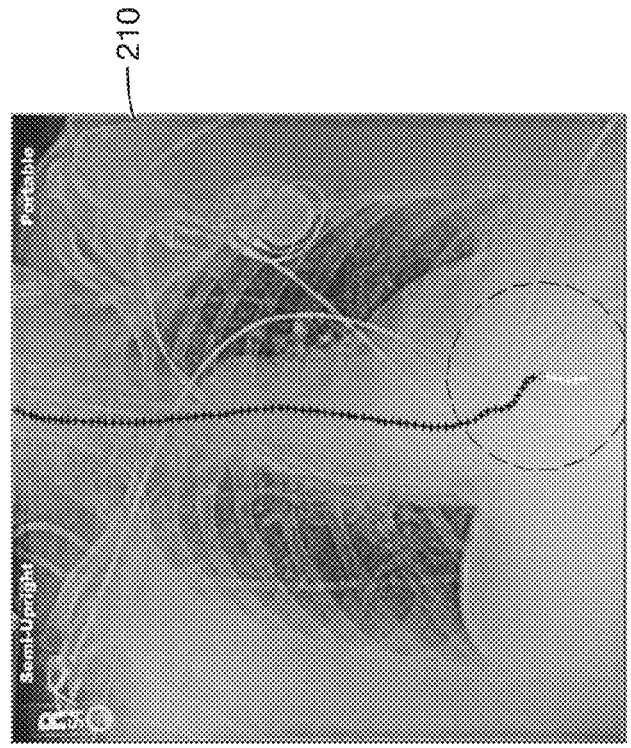
Figure 18C:
Figure 19A:
FIGS. 19A through 19E are images of sample results for K1=0.1 and K2=0.2 values for the ET Tube.
Figure 19C:
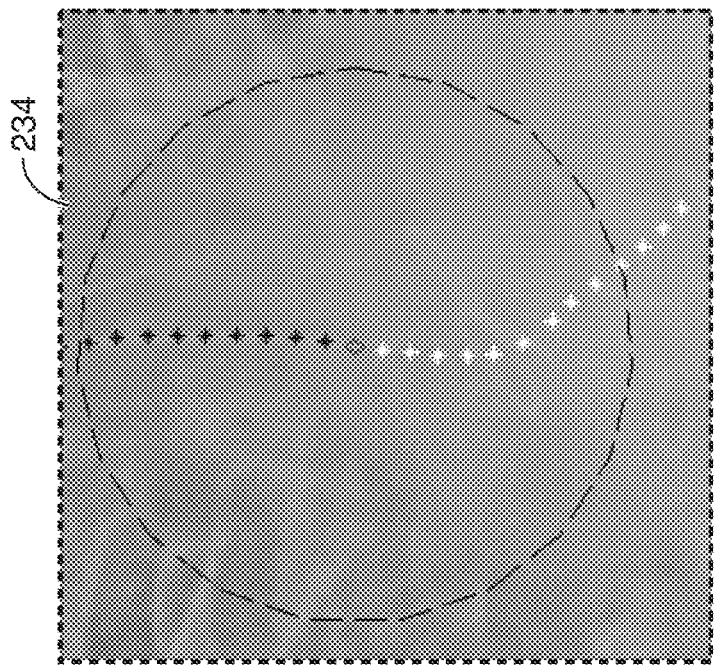
Figure 19B:
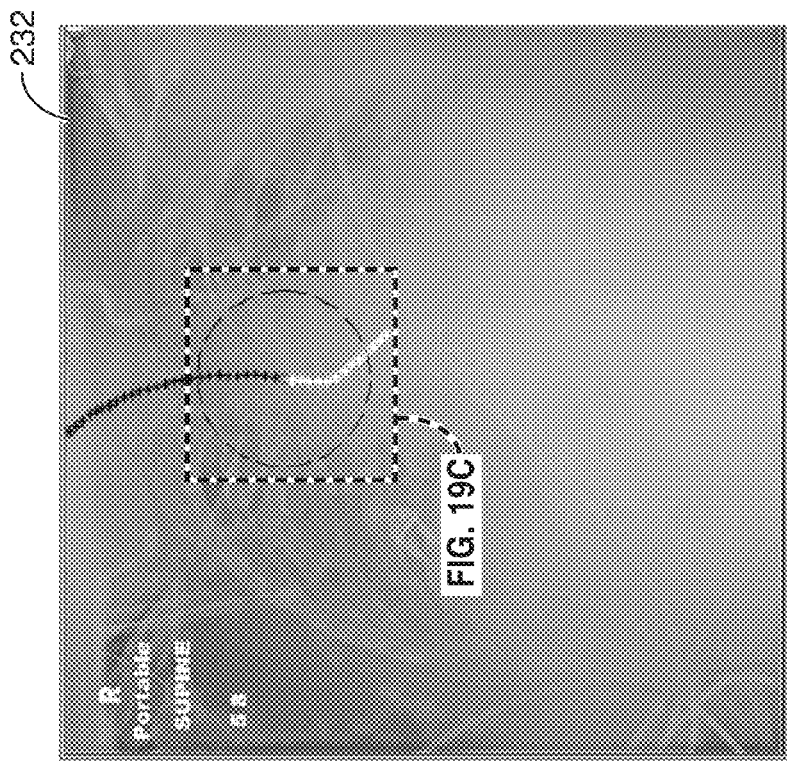
Figure 19E:
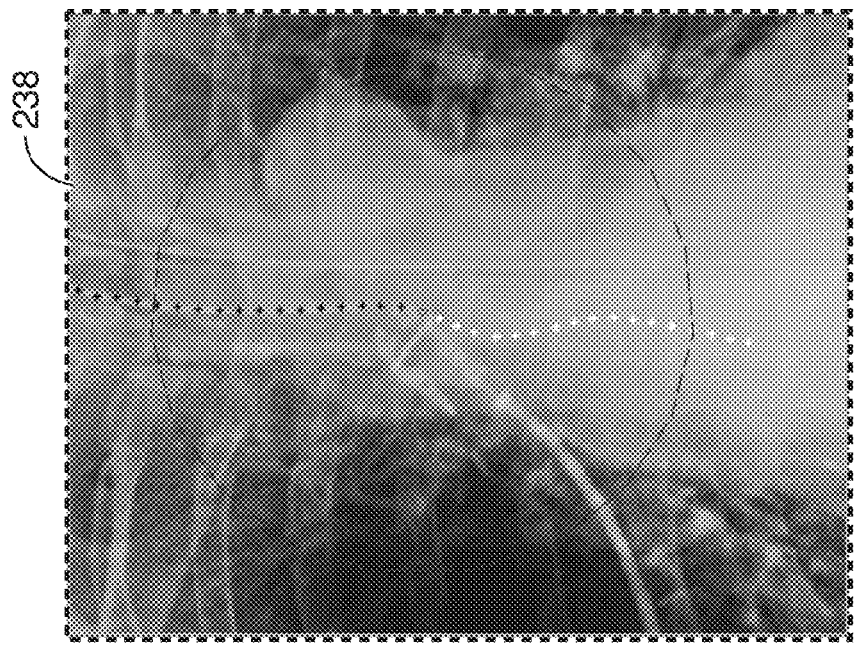
Figure 19D:
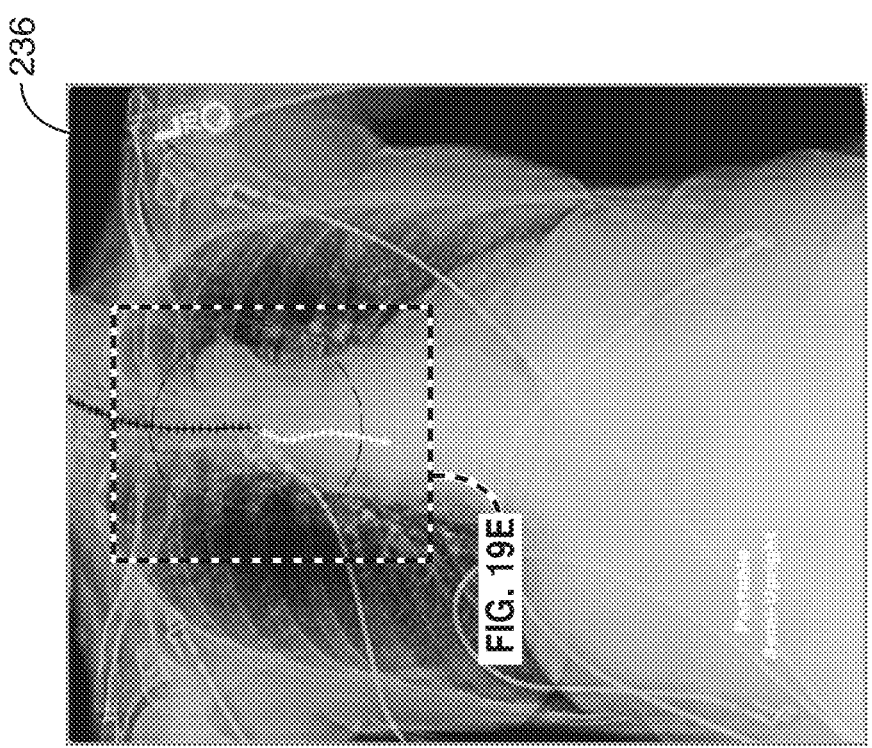

FIGS. 18A-C show regions of uncertainty for a set of images 210, 212, and 214 for specific values of $k_1$=0.2 and $k_2$=0.4 for the NG tube.

FIGS. 19A-E show regions of uncertainty (with FIGS. 19C and 19E being exploded views of the regions illustrated in FIGS. 19B and 19D respectively) showing for a set of images 230, 232, 234, 236 and 238 for specific values of $k_1$=0.1 and $k_2$=0.2 for the ET tube.

Figure 20:
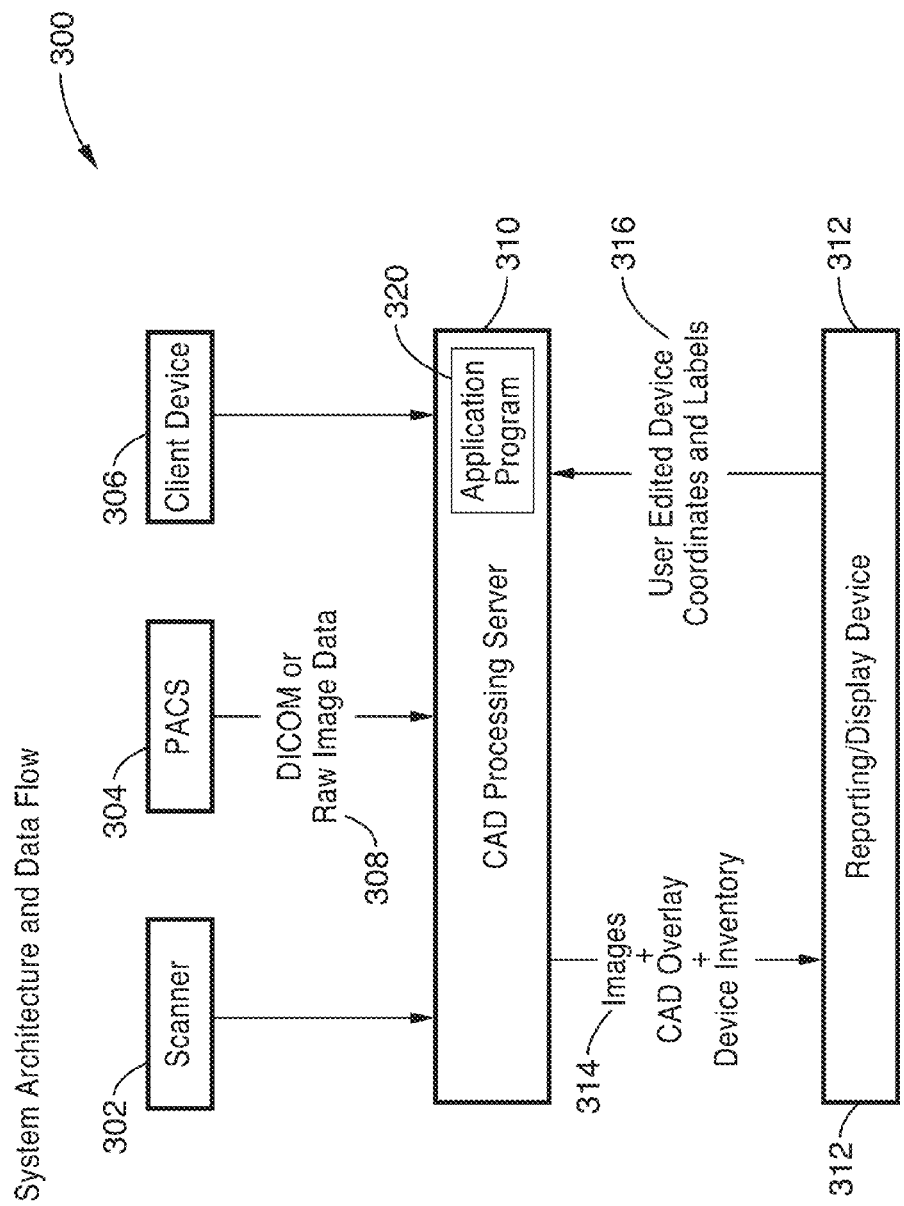
FIG. 20 shows a schematic diagram of a CAD detection system in accordance with the present invention.

FIG. 20 shows a schematic diagram of a CAD detection system 300 and data flow in accordance with the present invention. In a preferred embodiment, the CAD system 300 and method 10 of the present invention are implemented as computer software via application program or detection module 320. This software 320 may be run on an individual medical imaging workstation, either at the image acquisition device (e.g. scanner 302) or on a reading workstation. The software may also be run on a centralized server or cluster of servers in a radiology department or medical center (e.g. CAD processing server 310). It is appreciated that application software may be run on any device or computer having a processor configured for executing the software module 320. Running on a server 310 may provide advantages in terms of interfacing with a centralized imaging archive PACS 304 (picture archiving and communication system) for retrieving DICOM or raw image data 308, and storing CAD-IMD reports in a centralized database.

The system 300 may also be accessed remotely (via the internet), for example, using GRID computing for view at one or more client devices 306. Using this approach the system 300 is made available as a GRID service and clients with proper authentication/authorization can access it worldwide.

Following detection and classification of an IMD using method 10, the CAD system 300 is configured to automatically generate a report 314 via a reporting/display device 312. The report 314 may comprise images with CAD overlay, coordinates, measurements, region of uncertainty, and device inventory. The location of an IMD on a medical image 12 (e.g. with overlay step 24 in FIG. 1) may be displayed by markers on an image or by colorizing classified pixels. The IMD may also be extracted and rendered separately providing a 3D visualization. The type of device may be reported including manufacturer specifications, schematics, images, etc. The report 314 may also describe whether the imaged IMD is consistent with manufacturer's specifications. This may include visualization and comparison of the implanted device against manufacturer specifications ("out of the box images").

In one embodiment, report 314 may include a set of image features that are computed at the pixel or patch level, including intensity (gray-level) and gradient profile computed at multiple scales. Features may also be computed and the object or region level, including shape, orientation and relative position in the image displayed. A pattern classifier may be compiled from an expert-segmented set of cases from which these features are calculated and expected values are machine learned. This classification model is then applied to new cases to automatically label pixels according to the type of IMD they represent.

Data 316 (e.g. user edited device coordinates and labels) may also be input to the server 310 and application program 320 from display device 312 for incremental CAD feedback machine learning. The display device 312 may comprise a computer workstation, handheld device, and support data transfer protocols including DICOM, FTP, sFTP, HTTP, HTTPs, RTSP, etc.

Figures 21A, 21B:
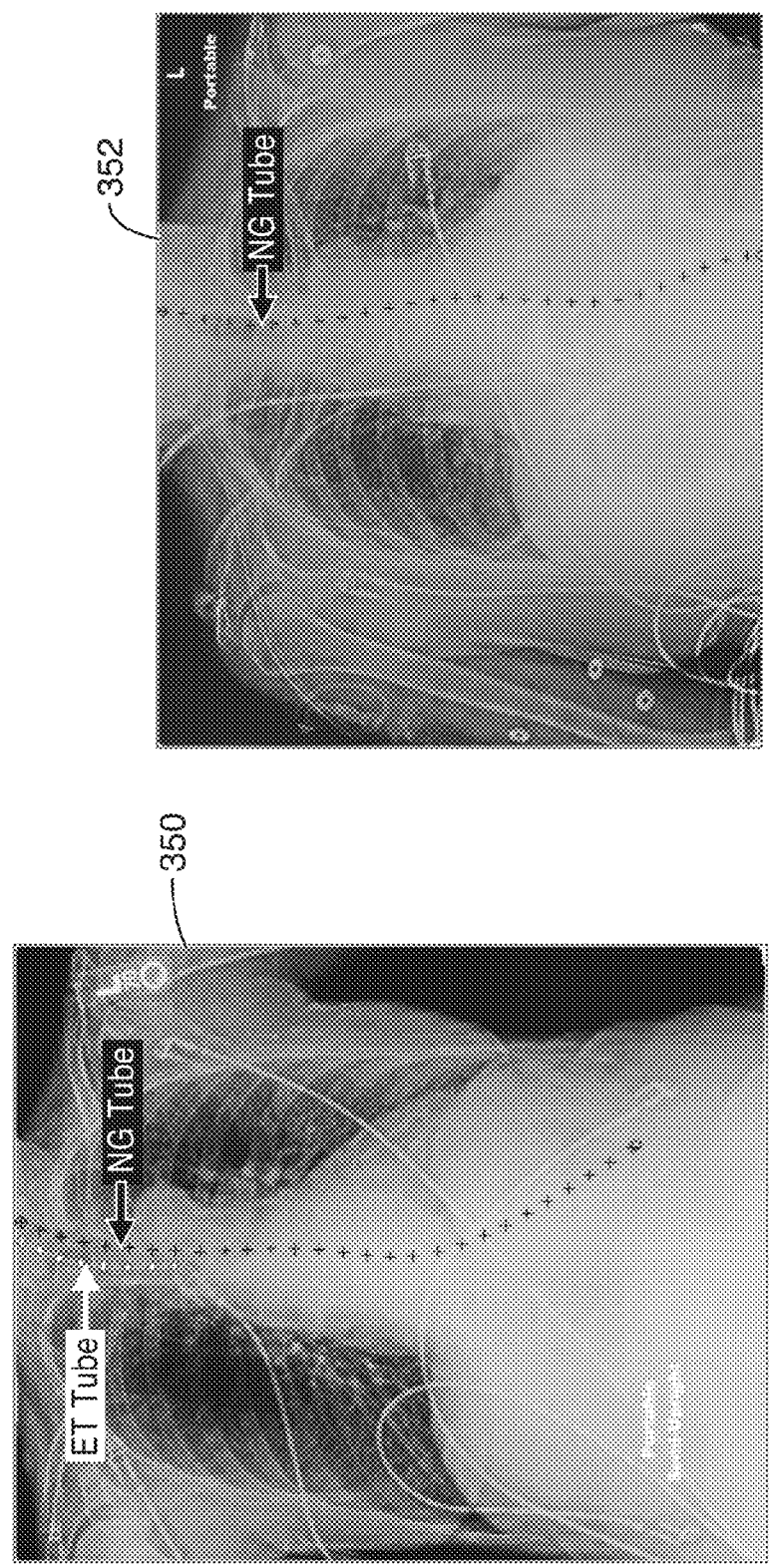
FIGS. 21A through 21F show sample images showing results from the CAD system of the present invention.
Figure 21D:
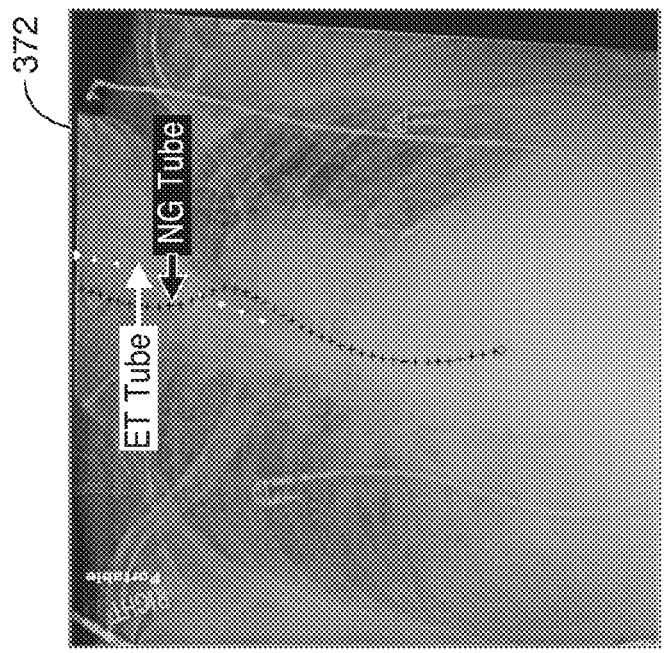
Figure 21C:
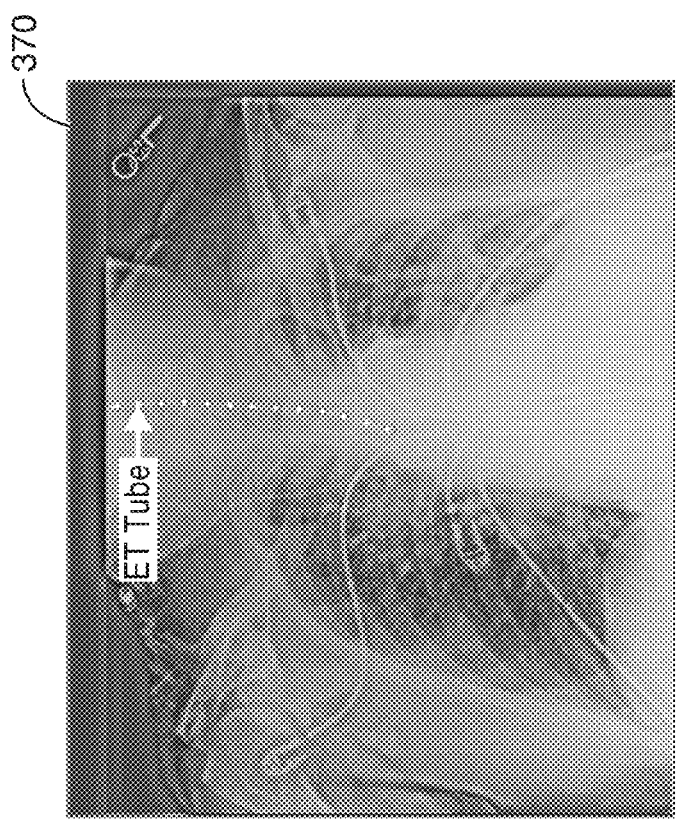

The system 300 and method 10 were also tested to determine efficacy. FIGS. 21A through 21F are sample images showing results from the CAD system 300 and method 10 of the present invention. Sixty-four chest radiographs were identified and obtained from 52 patients. Of these, 20 had both ET tube and NG tubes, 5 with only NG Tube, 8 with only ET tube, and 31 had no tubes. The CAD system performance is shown in Table 1 for ET tube and NG tubes respectively. The CAD system was able to detect ET tubes with a True Positive Rate (TPR) of 0.93 and False Positive Rate (FPR) of 0.02/image. For the NG tube, the True Positive Rate (TPR) was 0.84 and False Positive Rate of 0.02/image. FIG. 21A shows image 350 where both the ET tube and NG tube were detected. FIG. 21B shows image 352 where the NG tube was detected. FIG. 21C shows image 370 where the ET tube was detected. FIG. 21D shows image 372 where both the ET tube and NG tube were detected.

Figure 21F:
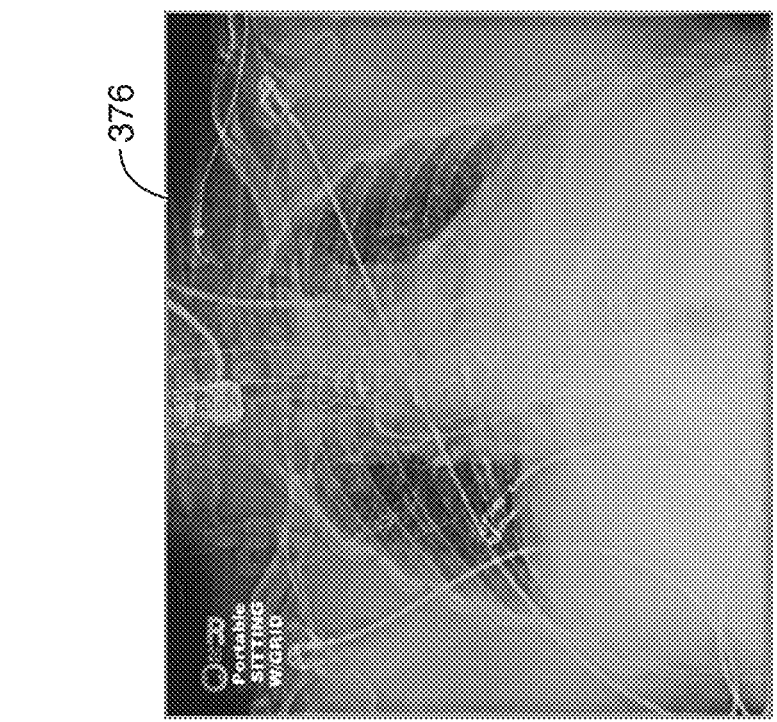
Figure 21E:
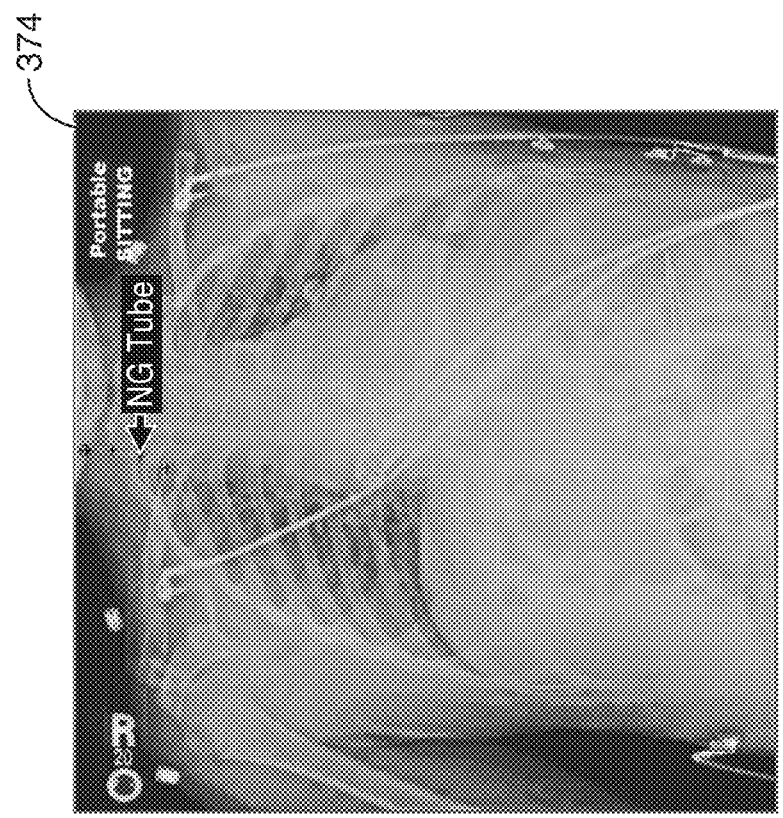

FIG. 21E shows image 374 where an NG tube was wrongly detected (false positive). FIG. 21F shows image 376 where both the ET tube and NG tube were present but not detected. The cases where the CAD system failed to detect tubes were primarily caused by multiple tubes in close proximity as seen in FIG. 21F.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula (e), or computational depiction(s).

From the discussion above it will be appreciated that the invention can be embodied in various ways, including the following:

1. A computer automated detection method for detection of one or more implantable man-made devices (IMD's) within the body of a patient, comprising: receiving an image of the patient; segmenting the image into one or more regions of interest, the regions of interest corresponding to anatomical features of the patient; generating one or more seed points from a designated region of interest from the one or more regions of interest in the segmented image; projecting one or more grown seed points along a path based on the one or more generated seeds; and overlaying an IMD position based on the grown seed path over the patient image.

2. The method of embodiment 1, wherein image comprises a radiograph.

3. The method of embodiment 1: wherein the one or more IMD comprises a catheter; and wherein generating one or more seed points comprises: detecting a pair of parallel lines; calculating a midpoint between the pair of parallel lines; and assigning a location of one of said one or more seed points at said midpoint.

4. The method of embodiment 3, wherein projecting one or more grown seed points comprises: matching one or more templates of the catheter with the one or more seed points; and growing the path of the one or more seed points as a function of a profile of the catheter.

5. The method of embodiment 4, wherein the template comprises orientation, translation and tube profiles as parameters used in growing the path of the one or more seed points.

6. The method of embodiment 5, further comprising: calculating a template match score; the template match score corresponding to confidence that a new point lies within an expected path of the generated seeds; wherein the growth of the path of the one or more seed points is stopped upon the template match score falling below a threshold value.

7. The method of embodiment 5, further comprising: selecting a path from a plurality of grown paths; said selected path corresponding to a predetermined catheter profile; and overlaying a catheter profile at the position within the image based on the selected path.

8. The method of embodiment 3: wherein catheter comprises one or more of a NG tube or ET tube; and wherein one of the one or more regions of interest comprises a region of the neck of the patient; wherein the one or more seeds are generated within the neck region of interest.

9. The method of embodiment 3: wherein catheter comprises a CVC tube; wherein one of the one or more regions of interest comprises a heart region of interest and a lung region of interest; and wherein the one or more seeds are generated within the heart region of interest and grown toward the lung region of interest.

10. A computer automated detection apparatus for detection of one or more implantable man-made devices (IMD's) within the body of a patient, comprising: a processor; and programming executable on said processor for: receiving an image of the patient; segmenting the image into one or more regions of interest, the regions of interest corresponding to anatomical features of the patient; generating one or more seed points from the a designated region of interest from the one or more regions of interest in the segmented image; projecting one or more grown seed points along a path based on the one or more generated seeds; and overlaying an IMD position based on the grown seed path over the patient image.

11. The apparatus of embodiment 10, wherein image comprises a radiograph.

12. The apparatus of embodiment 10: wherein the one or more IMD comprises a catheter; and wherein generating one or more seed points comprises: detecting a pair of parallel lines; calculating a midpoint between the pair of parallel lines; and assigning a location of one of said one or more seed points at said midpoint.

13. The apparatus of embodiment 12, wherein projecting one or more grown seed points comprises: matching one or more templates of the catheter with the one or more seed points; and growing the path of the one or more seed points as a function of a profile of the catheter.

14. The apparatus of embodiment 12, wherein the template comprises orientation, translation and tube profiles as parameters used in growing the path of the one or more seed points.

15. The apparatus of embodiment 14, further comprising: calculating a template match score; the template match score corresponding to confidence that a new point lies within an expected path of the generated seeds; wherein the growth of the path of the one or more seed points is stopped upon the template match score falling below a threshold value.

16. The apparatus of embodiment 14, further comprising: selecting a path from a plurality of grown paths; said selected path corresponding to a predetermined catheter profile; and overlaying a catheter profile at the position within the image based on the selected path.

17. The apparatus of embodiment 12: wherein catheter comprises one or more of a NG tube or ET tube; wherein one of the one or more regions of interest comprises a region of the neck of the patient; and wherein the one or more seeds are generated within the neck region of interest.

18. The apparatus of embodiment 12: wherein catheter comprises a CVC tube; wherein one of the one or more regions of interest comprises a heart region of interest and a lung region of interest; and wherein the one or more seeds are generated within the heart region of interest and grown toward the lung region of interest.

19. A detection apparatus for automatically detecting one or more implantable man-made devices (IMD's) within the body of a patient, comprising: a scanner; the scanner configured for generating an image of the patient; and a detection module coupled to the scanner, the module configured for: receiving the image of the patient; segmenting the image into one or more regions of interest, the regions of interest corresponding to anatomical features of the patient; generating one or more seed points from the designated region of interest in the segmented image; projecting one or more grown seed points along a path based on the one or more generated seeds; and overlaying an IMD position based on the grown seed path over the patient image.

20. The apparatus of embodiment 19, wherein image comprises a radiograph.

21. The apparatus of embodiment 19: wherein the one or more IMD comprises a catheter; and wherein generating one or more seed points comprises: detecting a pair of parallel lines; calculating a midpoint between the pair of parallel lines; and assigning a location of one of said one or more seed points at said midpoint.

22. The apparatus of embodiment 21, wherein projecting one or more grown seed points comprises: matching one or more templates of the catheter with the one or more seed points; and growing the path of the one or more seed points as a function of a profile of the catheter.

23. The apparatus of embodiment 21, wherein the template comprises orientation, translation and tube profiles as parameters used in growing the path of the one or more seed points.

24. The apparatus of embodiment 23, further comprising: calculating a template match score; the template match score corresponding to confidence that a new point lies within an expected path of the generated seeds; wherein the growth of the path of the one or more seed points is stopped upon the template match score falling below a threshold value.

25. The apparatus of embodiment 23, further comprising: selecting a path from a plurality of grown paths; said selected path corresponding to a predetermined catheter profile; and overlaying a catheter profile at the position within the image based on the selected path.

26. The apparatus of embodiment 21: wherein catheter comprises one or more of a NG tube or ET tube; wherein one of the one or more regions of interest comprises a region of the neck of the patient; and wherein the one or more seeds are generated within the neck region of interest.

27. The apparatus of embodiment 21: wherein catheter comprises a CVC tube; wherein one of the one or more regions of interest comprises a heart region of interest and a lung region of interest; and wherein the one or more seeds are generated within the heart region of interest and grown toward the lung region of interest.

28. The apparatus of embodiment 19, wherein the detection module is configured for receiving user-edited results of IMD position and type for incremental machine learning.

29. A non-transitory computer readable media containing instructions executable on a computer for carrying out a method for detection of one or more implantable man-made devices (IMD's) within the body of a patient, the method comprising: receiving an image of the patient; segmenting the image into one or more regions of interest, the regions of interest corresponding to anatomical features of the patient; generating one or more seed points from the a designated region of interest from the one or more regions of interest in the segmented image; projecting one or more grown seed points along a path based on the one or more generated seeds; and overlaying an IMD position based on the grown seed path over the patient image.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

CAD System performance (Number of True Positives & False Positives)

| Tube Type | True Positives | False Positives |
|---|---|---|
| ET | 26 | 1 |
| NG | 21 | 1 |

What is claimed is:

1. A computer automated detection method for detection of one or more implantable man-made devices (IMD's) within the body of a patient, comprising:
   receiving an image of the patient;
   segmenting the image into one or more regions of interest, the regions of interest corresponding to anatomical features of the patient;
   generating one or more seed points from a designated region of interest from the one or more regions of interest in the segmented image;
   projecting one or more grown seed points along a path based on the one or more generated seeds; and
   overlaying an IMD position based on the grown seed path over the patient image;
   wherein the overlaid IMD position comprises an IMD path that follows the grown seed path along the length of the IMD within the image;
   wherein the one or more IMD comprises a catheter comprising one or more of a NG tube or ET tube;
   wherein generating one or more seed points comprises:
     detecting a pair of parallel lines;
     calculating a midpoint between the pair of parallel lines; and
     assigning a location of one of said one or more seed points at said midpoint;
   wherein segmenting the image into one or more regions of interest comprises automatically detecting a region of the neck of the patient; and
   wherein the one or more seeds are generated within the neck region of interest.

2. The method recited in claim 1, wherein the image comprises a radiograph.

3. The method recited in claim 1, wherein projecting one or more grown seed points comprises:
   matching one or more templates of the catheter with the one or more seed points; and
   growing the path of the one or more seed points as a function of a profile of the catheter template;
   wherein the catheter template profile is dynamically applied at each seed point based on at least one prior seed point location in the grown path.

4. The method recited in claim 1, wherein the template comprises orientation, translation and tube profiles as parameters used in growing the path of the one or more seed points; and
   wherein the orientation of the template is updated adaptively based on at least one prior seed point location in the grown path.

5. The method recited in claim 4, further comprising:
   calculating a template match score;
   the template match score corresponding to confidence that a new point lies within an expected path of the generated seeds;
   wherein the growth of the path of the one or more seed points is stopped upon the template match score falling below a threshold value.

6. The method recited in claim 4, further comprising:
   selecting a path from a plurality of grown paths, each of said grown paths being from a distinct starting position;
   said selected path corresponding to a predetermined catheter profile; and
   overlaying a catheter profile at the position within the image based on the selected path.

7. The method recited in claim 1:
   wherein catheter comprises a CVC tube;
   wherein the one or more regions of interest comprises a heart region of interest and a lung region of interest; and
   wherein the one or more seeds are generated within the heart region of interest and grown toward the lung region of interest.

8. A computer automated detection apparatus for detection of one or more implantable man-made devices (IMD's) within the body of a patient, comprising:
   a processor; and
   programming executable on said processor for:
     receiving an image of the patient;
     segmenting the image into one or more regions of interest, the regions of interest corresponding to anatomical features of the patient;
     generating one or more seed points from the a designated region of interest from the one or more regions of interest in the segmented image;
     projecting one or more grown seed points along a path based on the one or more generated seeds; and
     overlaying an IMD position based on the grown seed path over the patient image;
     wherein the overlaid IMD position comprises an IMD path that follows the grown seed path along the length of the IMD within the image;
     wherein the one or more IMD comprises a catheter comprising one or more of a NG tube or ET tube;
     wherein generating one or more seed points comprises:
       detecting a pair of parallel lines;
       calculating a midpoint between the pair of parallel lines; and
       assigning a location of one of said one or more seed points at said midpoint;
     wherein segmenting the image into one or more regions of interest comprises automatically detecting a region of the neck of the patient; and
     wherein the one or more seeds are generated within the neck region of interest.

9. The apparatus recited in claim 8, wherein the image comprises a radiograph.

10. The apparatus recited in claim 8, wherein projecting one or more grown seed points comprises:
    matching one or more templates of the catheter with the one or more seed points; and
    growing the path of the one or more seed points as a function of a profile of the catheter template;

wherein the catheter template profile is dynamically applied at each seed point based on at least one prior seed point location in the grown path.

11. The apparatus recited in claim 10, wherein the template comprises orientation, translation and tube profiles as parameters used in growing the path of the one or more seed points; and
wherein the orientation of the template is updated adaptively based on at least one prior seed point location in the grown path.

12. The apparatus recited in claim 11, further comprising:
calculating a template match score;
the template match score corresponding to confidence that a new point lies within an expected path of the generated seeds;
wherein the growth of the path of the one or more seed points is stopped upon the template match score falling below a threshold value.

13. The apparatus recited in claim 11, further comprising:
selecting a path from a plurality of grown paths, each of said grown paths being from a distinct starting position;
said selected path corresponding to a predetermined catheter profile; and
overlaying a catheter profile at the position within the image based on the selected path.

14. The apparatus recited in claim 8:
wherein catheter comprises a CVC tube;
wherein the one or more regions of interest comprises a heart region of interest and a lung region of interest; and
wherein the one or more seeds are generated within the heart region of interest and grown toward the lung region of interest.

15. A detection apparatus for automatically detecting one or more implantable man-made devices (IMD's) within the body of a patient, comprising:
a scanner;
the scanner configured for generating an image of the patient; and
a detection module coupled to the scanner, the module configured for:
receiving the image of the patient;
segmenting the image into one or more regions of interest, the regions of interest corresponding to anatomical features of the patient;
generating one or more seed points from the designated region of interest in the segmented image;
projecting one or more grown seed points along a path based on the one or more generated seeds; and
overlaying an IMD position based on the grown seed path over the patient image;
wherein the overlaid IMD position comprises an IMD path that follows the grown seed path along the length of the IMD within the image;
wherein the one or more IMD comprises a catheter;
wherein generating one or more seed points comprises:
detecting a pair of parallel lines;
calculating a midpoint between the pair of parallel lines; and
assigning a location of one of said one or more seed points at said midpoint;
wherein projecting one or more grown seed points comprises:
matching one or more templates of the catheter with the one or more seed points; and
growing the path of the one or more seed points as a function of a profile of the catheter template;
wherein the catheter template profile is dynamically applied at each seed point based on at least one prior seed point location in the grown path;
wherein the template comprises orientation, translation and tube profiles as parameters used in growing the path of the one or more seed points; and
wherein the orientation of the template is updated adaptively based on at least one prior seed point location in the grown path.

16. The apparatus recited in claim 15, wherein the image comprises a radiograph.

17. The apparatus recited in claim 15, further comprising:
calculating a template match score;
the template match score corresponding to confidence that a new point lies within an expected path of the generated seeds;
wherein the growth of the path of the one or more seed points is stopped upon the template match score falling below a threshold value.

18. The apparatus recited in claim 15, further comprising:
selecting a path from a plurality of grown paths, each of said grown paths being from a distinct starting position;
said selected path corresponding to a predetermined catheter profile; and
overlaying a catheter profile at the position within the image based on the selected path.

19. The apparatus recited in claim 15:
wherein catheter comprises one or more of a NG tube or ET tube;
wherein segmenting the image into one or more regions of interest comprises automatically detecting a region of the neck of the patient; and
wherein the one or more seeds are generated within the neck region of interest.

20. The apparatus recited in claim 15:
wherein catheter comprises a CVC tube;
wherein the one or more regions of interest comprises a heart region of interest and a lung region of interest; and
wherein the one or more seeds are generated within the heart region of interest and grown toward the lung region of interest.

21. The apparatus recited in claim 15, wherein the detection module is configured for receiving user-edited results of IMD position and type for incremental machine learning.

22. A computer automated detection method for detection of one or more implantable man-made devices (IMD's) within the body of a patient, comprising:
receiving an image of the patient;
segmenting the image into one or more regions of interest, the regions of interest corresponding to anatomical features of the patient;
generating one or more seed points from a designated region of interest from the one or more regions of interest in the segmented image;
projecting one or more grown seed points along a path based on the one or more generated seeds; and
overlaying an IMD position based on the grown seed path over the patient image; wherein the overlaid IMD position comprises an IMD path that follows the grown seed path along the length of the IMD within the image;
wherein the one or more IMD comprises a catheter;
wherein generating one or more seed points comprises:
detecting a pair of parallel lines;
calculating a midpoint between the pair of parallel lines; and assigning a location of one of said one or more seed points at said midpoint;
wherein projecting one or more grown seed points comprises:
   matching one or more templates of the catheter with the one or more seed points; and
   growing the path of the one or more seed points as a function of a profile of the catheter template;
wherein the catheter template profile is dynamically applied at each seed point based on at least one prior seed point location in the grown path;
wherein the template comprises orientation, translation and tube profiles as parameters used in growing the path of the one or more seed points; and
wherein the orientation of the template is updated adaptively based on at least one prior seed point location in the grown path.

23. A computer automated detection apparatus for detection of one or more implantable man-made devices (IMD's) within the body of a patient, comprising:
a processor; and
programming executable on said processor for:
   receiving an image of the patient;
   segmenting the image into one or more regions of interest, the regions of interest corresponding to anatomical features of the patient;
   generating one or more seed points from the a designated region of interest from the one or more regions of interest in the segmented image;
   projecting one or more grown seed points along a path based on the one or more generated seeds; and
   overlaying an IMD position based on the grown seed path over the patient image;
wherein the overlaid IMD position comprises an IMD path that follows the grown seed path along the length of the IMD within the image;
wherein the one or more IMD comprises a catheter;
wherein generating one or more seed points comprises:
   detecting a pair of parallel lines;
   calculating a midpoint between the pair of parallel lines; and
   assigning a location of one of said one or more seed points at said midpoint;
wherein projecting one or more grown seed points comprises:
   matching one or more templates of the catheter with the one or more seed points; and
   growing the path of the one or more seed points as a function of a profile of the catheter template;
wherein the catheter template profile is dynamically applied at each seed point based on at least one prior seed point location in the grown path;
wherein the template comprises orientation, translation and tube profiles as parameters used in growing the path of the one or more seed points; and
wherein the orientation of the template is updated adaptively based on at least one prior seed point location in the grown path.

24. A detection apparatus for automatically detecting one or more implantable man-made devices (IMD's) within the body of a patient, comprising:
a scanner;
the scanner configured for generating an image of the patient; and
a detection module coupled to the scanner, the module configured for:
   receiving the image of the patient;
   segmenting the image into one or more regions of interest, the regions of interest corresponding to anatomical features of the patient;
   generating one or more seed points from the designated region of interest in the segmented image;
   projecting one or more grown seed points along a path based on the one or more generated seeds; and
   overlaying an IMD position based on the grown seed path over the patient image;
   wherein the overlaid IMD position comprises an IMD path that follows the grown seed path along the length of the IMD within the image;
wherein the one or more IMD comprises a catheter; and
wherein generating one or more seed points comprises:
   detecting a pair of parallel lines;
   calculating a midpoint between the pair of parallel lines; and
   assigning a location of one of said one or more seed points at said midpoint;
wherein catheter comprises one or more of a NG tube or ET tube;
wherein segmenting the image into one or more regions of interest comprises automatically detecting a region of the neck of the patient; and
wherein the one or more seeds are generated within the neck region of interest.

* * * * *